US011759566B2

(12) United States Patent
Bertram et al.

(10) Patent No.: US 11,759,566 B2
(45) Date of Patent: Sep. 19, 2023

(54) DISTRIBUTION SYSTEM FOR FLOW CONTROL OF INFUSATE FROM BRANCH CATHETERS TO SELECTED SITE

(71) Applicant: University of Virginia Patent Foundation, Charlottesville, VA (US)

(72) Inventors: Edward H. Bertram, Charlottesville, VA (US); Nathan Swami, Charlottesville, VA (US); Walter Varhue, Glen Allen, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 197 days.

(21) Appl. No.: 17/050,082

(22) PCT Filed: May 29, 2019

(86) PCT No.: PCT/US2019/034378
§ 371 (c)(1),
(2) Date: Oct. 23, 2020

(87) PCT Pub. No.: WO2019/232035
PCT Pub. Date: Dec. 5, 2019

(65) Prior Publication Data
US 2021/0093778 A1    Apr. 1, 2021

Related U.S. Application Data

(60) Provisional application No. 62/678,518, filed on May 31, 2018.

(51) Int. Cl.
*A61M 5/168* (2006.01)
*A61M 5/142* (2006.01)
*A61M 25/02* (2006.01)

(52) U.S. Cl.
CPC ........ *A61M 5/16813* (2013.01); *A61M 5/142* (2013.01); *A61M 25/02* (2013.01);
(Continued)

(58) Field of Classification Search
CPC .. A61M 2025/0057; A61M 2210/0693; A61M 2205/84
See application file for complete search history.

(56) References Cited

U.S. PATENT DOCUMENTS

| 5,125,888 A | 6/1992 | Howard et al. |
| 5,707,335 A | 1/1998 | Howard et al. |

(Continued)

FOREIGN PATENT DOCUMENTS

WO    2007042999 A2    4/2007

OTHER PUBLICATIONS

Jahangiri, Arman, et al., "Convection-enhanced delivery in glioblastoma: a review of preclinical and clinical studies", Journal of Neurosurgery, 2017, vol. 126, pp. 191-200.
(Continued)

*Primary Examiner* — Deanna K Hall
(74) *Attorney, Agent, or Firm* — Robert J. Decker

(57) ABSTRACT

System and method to improve drug delivery to identified regions in the brain or elsewhere through direct infusion of a therapeutic agent or the like into that region. This direct infusion will allow for greater concentrations of the agent in the target region while reducing concentrations elsewhere in the body where these agents may be toxic. The system and method improves efficacy while reducing unwanted side effects. The system includes an array of multiple, independently targeted, microporous catheters for insertion into the target region and a distribution system that allows for individualized flow control to each catheter. The system may be connected to a reservoir that contains the therapeutic (Continued)

agent, and flow to the system is maintained through one or more pumps. This system will greatly improve on the current single catheter infusion design and shall provide therapy, delivered through multiple catheters, thus delivering the therapy evenly over a customizable volume.

30 Claims, 12 Drawing Sheets

(52) U.S. Cl.
CPC ............. *A61M 2025/024* (2013.01); *A61M 2205/3334* (2013.01); *A61M 2205/52* (2013.01); *A61M 2210/0693* (2013.01)

(56) References Cited

U.S. PATENT DOCUMENTS

| | | | |
|---|---|---|---|
| 5,779,694 | A | 7/1998 | Howard et al. |
| 6,027,487 | A | 2/2000 | Crocker |
| 6,093,180 | A | 7/2000 | Elsberry |
| 6,216,030 | B1 | 4/2001 | Howard et al. |
| 6,272,370 | B1 | 8/2001 | Gillies et al. |
| 6,298,259 | B1 | 10/2001 | Kucharczyk et al. |
| 6,524,300 | B2 | 2/2003 | Meglin |
| 6,551,290 | B1 | 4/2003 | Elsberry |
| 6,594,880 | B2 | 7/2003 | Elsberry |
| 6,599,274 | B1 | 7/2003 | Kucharczyk et al. |
| 6,626,902 | B1 | 9/2003 | Kucharczyk et al. |
| 6,834,201 | B2 | 12/2004 | Gillies et al. |
| 6,893,429 | B2 | 5/2005 | Petersen |
| 7,069,634 | B1 | 7/2006 | Elsberry |
| 7,670,327 | B2 | 3/2010 | Kucharczyk et al. |
| 7,727,225 | B2 | 6/2010 | Broaddus et al. |
| 8,043,281 | B2 | 10/2011 | Heruth et al. |
| 8,096,984 | B2 | 1/2012 | Kucharczyk et al. |
| 8,211,083 | B2 | 7/2012 | Broaddus et al. |
| 8,216,177 | B2 | 7/2012 | Heruth et al. |
| 8,226,694 | B2 | 7/2012 | Broaddus et al. |
| 8,255,193 | B2 | 8/2012 | Humphrey et al. |
| 8,267,905 | B2 | 9/2012 | Lobl et al. |
| 8,406,837 | B2 | 3/2013 | Gillies et al. |
| 8,480,626 | B2 | 7/2013 | Nelson |
| 8,545,477 | B2 | 10/2013 | Burke et al. |
| 8,551,044 | B2 | 10/2013 | Burke et al. |
| 8,655,798 | B2 | 2/2014 | Humphrey et al. |
| 8,728,053 | B2 | 5/2014 | Broaddus et al. |
| 8,808,234 | B2 | 8/2014 | Vogelbaum et al. |
| 8,932,270 | B2 | 1/2015 | O'Day |
| 8,945,089 | B2 | 2/2015 | Johnson et al. |
| 8,979,822 | B2 | 3/2015 | Vogelbaum et al. |
| 9,352,117 | B2 | 5/2016 | O'Day |
| 9,669,198 | B2 | 6/2017 | Broaddus et al. |
| 10,159,782 | B2 | 12/2018 | Elias et al. |
| 2003/0045866 | A1* | 3/2003 | Petersen ............ A61M 25/0043 604/9 |
| 2004/0220547 | A1 | 11/2004 | Heruth et al. |
| 2006/0229573 | A1 | 10/2006 | Lamborne |
| 2009/0048577 | A1* | 2/2009 | Gillies .................. A61B 5/064 600/420 |
| 2013/0267928 | A1* | 10/2013 | Imran ............... A61M 37/0069 604/500 |
| 2016/0166803 | A1 | 6/2016 | Massi et al. |
| 2018/0264191 | A1 | 9/2018 | Dagdeviren et al. |
| 2019/0070356 | A1 | 3/2019 | Elias et al. |

OTHER PUBLICATIONS

Langer, et al., "Ultrathin needle can deliver drugs directly to the brain", MIT News, Jan. 24, 2018, 2 pages.
Pham, Windy, "Neural implants modulate microstructures in the brain with pinpoint accuracy", MIT News, Jun. 28, 2018, 3 pages.
Prior, Julie, "McGovern Institute Neurotechnology (MINT) program funds three new projects", MIT News, Sep. 18, 2009, 3 pages.
Copenheaver, Blaine R., "International Search Report and Written Opinion of the International Searching Authority", International patent application No. PCT /US2019/034378, dated Aug. 16, 2019, 11 pages.
Nickitas-Etienne, Athina, "International Preliminary Report on Patentability", International patent application No. PCT/US2019/034378, dated Aug. 16, 2019, 1 page.
Au, Anthony K., et al., "Microvalves and Micropumps for BioMEMS", Micromachines, 2011, vol. 2, pp. 179-220.
Brenner, T., et al., "Frequency-dependent transversal flow control in centrifugal microfluidics", Lab on a Chip, 2005, vol. 5 No. 2, pp. 146-150.
Verson, Brian D., et al., "Recent advances in microscale pumping technologies: a review and evaluation", Microfluidics and Nanofluidics, 2008, vol. 5 No. 2, pp. 145-174.
Harbaugh RE, "Novel CNS-Directed Drug Delivery Systems in Alzheimer's Disease and Other Neurological Disorders", Neurobiology of Aging, 1989. Vol. 10, pp. 623-629.
Heiss, John D., et al., "Local distribution and toxicity of prolonged hippocampal infusion of muscimol.", J Neurosurg, 2005, vol. 103, pp. 1035-1045.
Iyer, Rajiv R., et al., "Tracking accuracy of T2- and diffusion-weighted magnetic resonance imaging for infusate distribution by convection-enhanced delivery", J Neurosurg, 2011, vol. 115, pp. 474-480.
Laser DJ. et al., "A review of micropumps" J. Micromech. Microeng, 2004, vol. 14, pages R35-R64.
Lewis Owen., et al., "Chronic, intermittent convection-enhanced delivery devices", Journal of Neuroscience Methods, 2016, vol. 259, pp. 47-56.
Madhankumar A.B., et al, "Interleukin-13 receptor-targeted nanovesicles are a potential therapy for glioblastoma multiforme", Mol Cancer Ther, Dec. 2006, vol. 5 No. 12, pp. 3162-3169.
Moufawad Sami, et al., "Intraspinal Drug Delivery for Chronic Pain and Spasticity: Anatomic and Physiologic Considerations", Seminars in Pain Medicine. 2003, vol. 1 No. 4.
Van Putten, Erik H.P., et al., "Magnetic Resonance Imaging Based Assessment of Gadolinium-Conjugated Diethylenetriamine Penta-Acetic Acid Test-Infusion in Detecting Dysfunction of Convection-Enhanced Delivery Catheters", World Neurosurg, 2016, vol. 89, pp. 272-279.
Rohani Ali, et al. "Quantifying spatio-temporal dynamics of biomarker pre-concentration and depletion in microfluidic systems by intensity threshold analysis", Biomicrofluidics vol. 8 No.5, 0522009, no date given.
Sampson, John H., et al., "Intracerebral infusion of an EGFR-targeted toxin in recurrent malignant brain tumors Neuro Oncol", 2008, vol. 10, pp. 320-329.
Sewing, A. Charlotte, et al., "Preclinical evaluation of convection-enhanced delivery of liposomal doxorubicin to treat pediatric diffuse intrinsic pontine glioma and thalamic high-grade glioma" J Neurosurg Pediatr, Feb. 17, 2017, vol. 19, pp. 518-530.
Sundararajan, Narayan, et al., "Microfluidic Operations Using Deformable Polymer Membranes Fabricated by Single Layer Soft Lithography", Lab Chip, Mars, 2005.
Van Schaeybroeck, et al., "Intrathecal baclofen for intractable cerebral spasticity: A prospective placebo-controlled, double-blind study", Neurosurgery 2000; vol. 46, pp. 603-612.

* cited by examiner

DISTRIBUTION SYSTEM FOR FLOW CONTROL OF INFUSATE FROM BRANCH CATHETERS TO SELECTED SITE

RELATED APPLICATIONS

The present application is a national stage filing of International Application No. PCT/US2019/034378, filed May 29, 2019, which claims benefit of priority under 35 U.S.C § 119 (e) from U.S. Provisional Application Ser. No. 62/678,518, filed May 31, 2018, entitled "Multicatheter System for Intracerebral Therapy Delivery and Related Method Thereof"; the disclosures of which are hereby incorporated by reference herein in their entirety.

FIELD OF INVENTION

The present disclosure relates generally to a distribution system of infusate to a subject, and more particularly a system to allow individualized or customized control of infusate to a selected site or multiple sites.

BACKGROUND

New therapy development for brain tumors is limited at present by the inability of most compounds to get into the brain from blood vessels through the blood brain barrier. The present inventor submits that delivery of these treatments directly into the brain tissue could bypass this major obstacle.

Malignant brain tumors (e.g. glioblastomas) are almost uniformly fatal, in part because, potentially effective drugs don't get into the brain. Direct injections into the tumor have not been successful in part because of the limited distribution from a single needle and from the brief, one time only exposure of the tumor to the drug.

Accordingly, an aspect of an embodiment of the present invention provides, among other things, a system and method for direct drug delivery into the tumor over longer periods of time so as to overcome these obstacles.

The current single end port catheters suffer from limited flow rates and rapid fall off in concentrations that reduce efficacy, especially in larger tumors. Flow rates that exceed a several microliters per minute result in reflux along the length of the catheter back to the surface so that much of the drug goes outside the target. Manufactured catheter side ports have variable, unpredictable flow resistance so, distribution of infusate through side ports is not uniform or predictable.

Therefore, there is a long felt need for a system to provide treatment directly into the brain tissue (or other sites) for optimum exposure, such as exposure time, exposure area and material flow rate, to a tumor (or other targeted region) and related methods thereof.

SUMMARY OF ASPECTS OF EMBODIMENTS OF THE INVENTION

An aspect of an embodiment of the present invention provides, among other things, a distribution system and related method to allow individualized or customized flow control of infusate to each of a plurality of branch catheters to a selected site or multiple sites.

An aspect of an embodiment of the present invention provides, among other things, a system and method that will deliver therapies directly to brain tumors or other targeted locations or regions.

In an embodiment, the present inventor has developed a new infusion catheter using microporous polytetrafluoroethylene-Teflon (PTFE-Teflon) that allows for even distribution along the length of the catheter that overcomes the current catheter limitations. An aspect of an embodiment of the present invention provides, among other things, an array of multiple microporous catheters that will create overlapping fields of drug concentrations and allow customizable therapeutic concentrations for tumors of different shapes and volumes. An intracerebral infusion array will require an integration of infusion catheter arrays under microfluidic flow control of the individual catheters. The present inventor's work demonstrates that such an array achieves a more even, broader distribution compared to a standard cannula.

An aspect of an embodiment of the present invention provides, among other things, a microfluidic control for consistent long term flow to multiple catheters in an array.

An aspect of an embodiment of the present invention provides, among other things, a distribution system and related method to improve drug delivery to identified regions in the brain or elsewhere through direct infusion of a therapeutic agent or the like into that region. The direct infusion, as provided aspects of embodiments of the present invention, will allow for greater concentrations of the agent in the target region while reducing concentrations elsewhere in the body where these agents may be toxic. This system and related approach shall improve efficacy while reducing unwanted side effects. One of the components of this drug delivery system includes an array of multiple, independently targeted, microporous catheters for insertion into the target region and a distribution system that allows for individualized flow control to each catheter. The distribution system may be connected to a reservoir that contains the therapeutic agent or the like, and flow to the system may be maintained through one or more pumps. This system will greatly improve on the current single catheter infusion design which has a distribution that is tightly restricted to a volume immediately adjacent to the catheter opening. Because, among other reasons, the therapy is delivered through multiple catheters the distribution system will deliver the therapy evenly over a customizable volume.

An aspect of an embodiment of the present invention provides, among other things, a distribution system to allow individualized or customized flow control of infusate to each of a plurality of branch catheters to a selected site of a subject. The distribution system may comprise a base catheter, configured for providing a passage for the infusate, supplied to the system, wherein the base catheter includes a supply end, a distal end, and an elongated body there between. The plurality of branch catheters may comprise a juncture end, a delivery end, and an elongated body there between, wherein a portion the elongated body comprises a region having a microporous structure; wherein the delivery ends provide an array of the plurality of the branch catheters wherein each of the plurality of the branch catheters, with their the microporous structure, are each configured to be independently inserted into the selected site of the subject to a specific inserted position, wherein the microporous structures are configured to allow the infusate to egress from the microporous structure to the selected site. The distribution system may comprises a micro flow control device in fluidic communication with each of the plurality of branch catheters; wherein the micro flow control device is configured to control, for each of the plurality of branch catheters, flow rate and volume of the infusate egressing from the microporous structure to the selected site in the specified inserted position.

An aspect of an embodiment of the present invention provides, among other things, a distribution system to allow individualized or customized flow control of infusate to each of a plurality of branch catheters to a selected site of a subject. The distribution system may comprise a base catheter, configured for providing a passage for the infusate, supplied to the system, the base catheter includes a supply end, a distal end, and an elongated body there between. The plurality of branch catheters may comprise a juncture end, a delivery end, and an elongated body there between, wherein a portion the elongated body comprises a region having a microporous structure. The distribution system may comprise a retainer device, configured to separate and hold each of the plurality of branch catheters; and wherein the delivery ends provide an array of the plurality of the branch catheters wherein each of the plurality of the branch catheters, with their the microporous structure, are held by the retainer device and separated from one another by the retainer device while being inserted into the selected site of the subject to a specific inserted position, wherein the microporous structures are configured to allow the infusate to egress from the microporous structure to the selected site. The distribution system may comprise a micro flow control device in fluidic communication with each of the plurality of branch catheters; wherein the micro flow control device is configured to control, for each of the plurality of branch catheters, flow rate and volume of the infusate egressing from the microporous structure to the selected site in the specified inserted position.

An aspect of an embodiment of the system (or components and subcomponents of the system) may be used multiple times in a single procedure and stored in a sterile container or environment until the specified time and place of use. Alternatively, the apparatus may be single use or disposable.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/operator/customer/client/server or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5). Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

An aspect of an embodiment of the present invention provides, among other things, the following: a surgical incision apparatus for puncturing a cutaneous layer of a subject for providing guided access to a subcutaneous organ or subcutaneous cavity of the subject. The apparatus may comprise: a retention body configured for securing a cutting tool therein, wherein the retention body having a distal end and proximal end; a housing configured for receiving the retention body, wherein the housing having a distal end and proximal end; a guidewire holder member disposed on the housing configured for receiving a guidewire therein and aligning with the guidewire to allow the cutting tool to travel along the guidewire; and wherein the retention body is configured to be movably attached relative to the housing to allow the distal end of the retention body to advance toward the subject to a deployed position.

An aspect of an embodiment of the present invention provides, among other things, the following: a surgical kit that may comprise a cutting tool; and a surgical incision apparatus, which may be used for puncturing a cutaneous layer of a subject for providing guided access to a subcutaneous organ or subcutaneous cavity of the subject. The surgical incision apparatus may comprise: a retention body configured for securing the cutting tool therein, wherein the retention body having a distal end and proximal end; a housing configured for receiving the retention body, wherein the housing having a distal end and proximal end; a guidewire holder member disposed on the housing configured for receiving a guidewire therein and aligning with the guidewire to allow the cutting tool to travel along the guidewire; and wherein the retention body is configured to be movably attached relative to the housing to allow the distal end of the retention body to advance toward the subject to a deployed position. The kit may further comprise a guidewire, other medical instrument, material or device, or the like.

An aspect of an embodiment of the present invention provides, among other things, the following: a surgical method for puncturing a cutaneous layer of a subject for providing guided access to a subcutaneous organ or subcutaneous cavity of the subject. The method may comprise: securing a cutting tool with a retention body; disposing the retention body with a housing; receiving a guidewire on the housing for aligning the housing with the guidewire; and advancing the retention body wherein the cutting tool travels along the guidewire and advances toward the subject to a deployed position to achieve the access to the subcutaneous organ or subcutaneous cavity of the subject. The method may also include magnetically attracting the guidewire (other medical instrument, material or device, or the like) toward the cutting tool while the cutting tool travels along the guidewire. The method may also include magnetically attracting the guidewire toward a magnet disposed on the retention body and/or housing.

An aspect of an embodiment of the present invention provides, among other things, a surgical incision apparatus and method for puncturing a cutaneous layer of a subject for providing guided access to a subcutaneous organ or subcutaneous cavity (or specified target region) of the subject. The apparatus may include a retention body configured for securing a cutting tool therein and a housing configured for receiving the retention body. The apparatus includes a guidewire holder member configured for receiving a guidewire therein and aligning with the guidewire to allow the cutting tool to travel along the guidewire. The retention body is configured to be movably attached relative to the housing to allow the retention body and cutting tool to advance toward the subject to a deployed position (or multiple deployed positions), and subsequently withdraw to a retracted position (or multiple retracted positions).

The invention itself, together with further objects and attendant advantages, will best be understood by reference to the following detailed description, taken in conjunction with the accompanying drawings.

These and other objects, along with advantages and features of various aspects of embodiments of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings.

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

FIG. 13 schematically illustrates an embodiment of the distribution system to allow individualized or customized flow control of infusate to each of a plurality of branch catheters to a selected site of a subject; and wherein at least one of a plurality of pumps and at least one of a plurality of flow sensors may be disposed on at least one of the plurality of branch catheters.

DETAILED DESCRIPTION OF EXEMPLARY EMBODIMENTS

Figure 1:
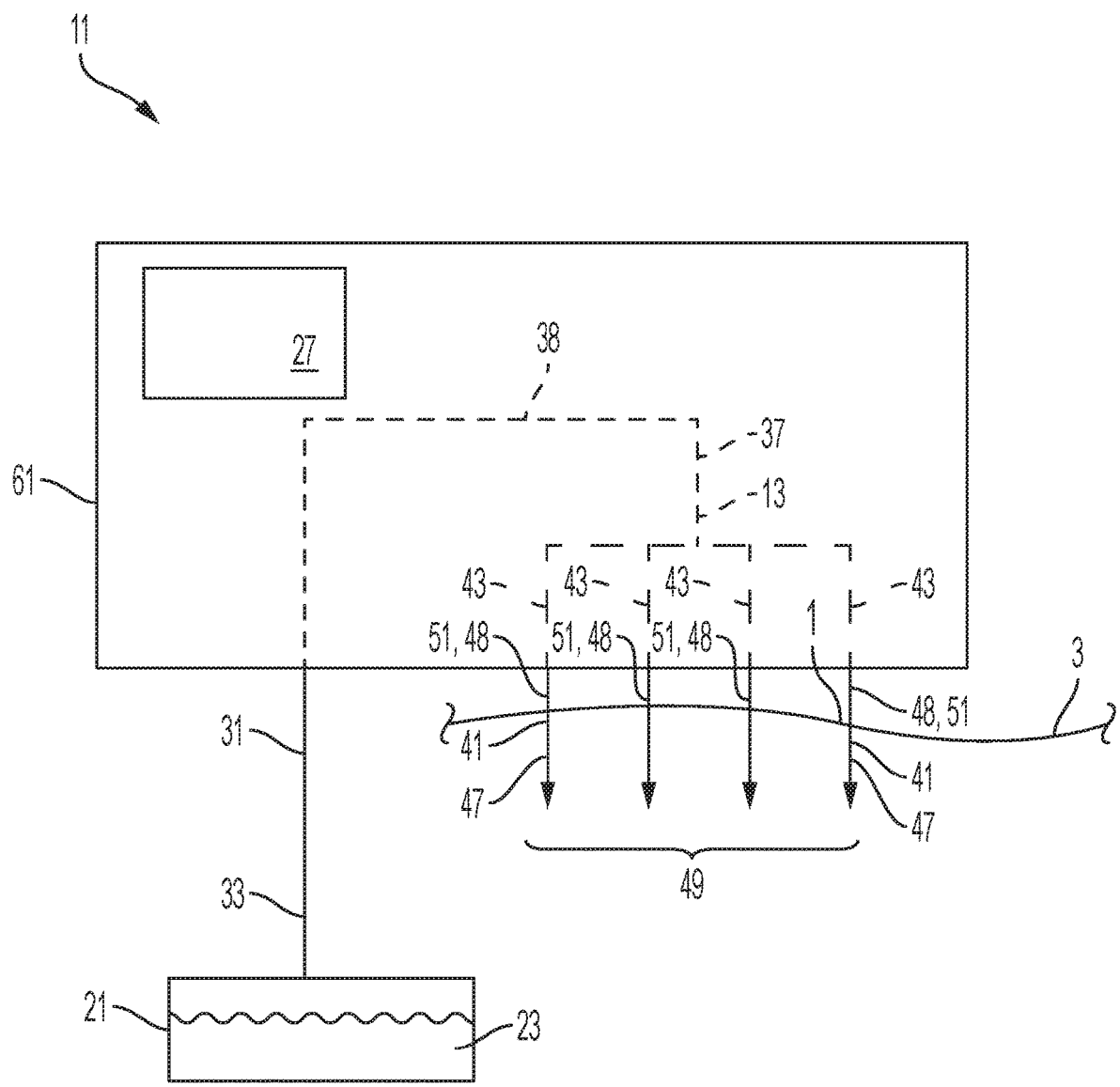
FIG. 1 schematically illustrates an embodiment of the distribution system to allow individualized or customized flow control of infusate to each of a plurality of branch catheters to a selected site of a subject.

Long-Felt Need or Problems (that Heretofore Unsolved)

There has been a long-felt need or problems (yet heretofore unsolved) that various aspects of embodiments of the invention disclosed herein addresses. Heretofore, it has been very difficult to get many potentially effective drugs past the blood brain barrier into the brain. Heretofore, it has been even more difficult to get those drugs to the part of the brain where they are needed and not to the other uninvolved regions of the brain. Effective, targeted drug delivery is an important goal that has not yet been achieved. The present inventor submits that malignant brain tumors and epilepsy are two important brain diseases that could benefit from drug delivery directly to the region of the brain responsible for the problem. The present inventor submits that direct delivery will also allow for the use of drugs that might be effective but which cannot cross the blood brain barrier. Accordingly, aspects of various embodiments of the invention disclosed herein allows for such direct delivery and also overcomes the recognized limitations of currently available infusion systems.

Unexpected Results and Discovery

Unexpected results and discovery occurred by the present inventor. The present inventor's early work suggested that direct infusion of drugs into well-defined regions in the brain could control seizures. However, initial work with standard infusion cannulas (single port at the tip of the cannula) demonstrated that absolute precision was needed for even small targets, because cannulas that were off target by as little as a millimeter were ineffective. The distribution of the infusate from this end port was restricted to the area around the tip with a rapid fall off in concentration so that the distribution of effective drug concentrations was spatially restricted. Attempts to overcome the problem by increased flow rate resulted in reflux along the length of the catheter so that most of the drug went back to the surface, away from the desired target. We and others also tried cannulas with multiple side ports to improve distribution along the cannula length, but we all have found that the distribution is unpredictable and uneven, as the side ports have variable resistance to flow so the distribution is typically predominantly around only a few of the ports. An aspect of various embodiments of the present invention arose from the many failures of current standard infusion technology to deliver an even drug distribution over the larger tissue volumes of tumors or seizure onset zones that would be needed to be effective. These performance requirements in light of the previous failures led to the decision to develop a system that would require arrays of multiple independently controlled cannulas using cannulas that would allow for an even distribution of material along its length. This latter feature would require an internal lumen with low flow resistance and multiple high flow resistance exit side ports that would allow for even distribution along the full length.

Prior Art and Conventional Wisdom Taught Away

Prior art or conventional wisdom taught away from the approach of various aspects of embodiments of the present invention. All of the designs tried by others to date have focused on single catheter infusion systems, usually for pain control. Although a few attempts have been made at treating brain tumors with direct injection of drugs, these were generally made with acute injections and no attempts have been made with longer term infusion. Drug infused wafers have also been used in tumor cavities, but there has been no consistent benefit, likely because the drug did not reach the areas distant to the wafer, which can also shift in position. The spinal infusion for pain and spasticity have been effective with infusion over many months, but the target has been relatively small and well defined. This situation is not the same for intracerebral targets which are often large and irregular in shape. The issue of insufficient and unpredictable distribution has also been recognized. One of the attempted solutions has been to increase flow rate (named convection enhanced delivery) with the hope that the increased volumes would reach a larger volume of tissue. There is a limit as to how much added fluid (high flow rates) can be absorbed by the surrounding tissue. As a result, as noted above (i.e., regarding the unexpected results and discovery section), this approach has resulted in reflux of the infusate along the cannula tract back to the brain surface as opposed to into the surrounding tissue. Convection enhanced delivery has largely been abandoned. To address this issue of greater diffusion into the surrounding tissue, a number of catheter designs have been provided with "manufactured" side ports (holes or slits cut into the catheter), but this approach suffers from the same issue of variable flow resistance across the ports with the consequence of unpredictable distribution of the infusate.

The conventional approach (common wisdom) was not working. The present inventor notes that past attempts that a single catheter, regardless of the catheter design, is insufficient. The present inventor notes that the multiple manufactured ports are not consistent in delivering an even drug distribution. Aspects of various embodiments of the present invention addresses both issues. In an embodiment, the design of the catheter may use available materials (for example, porous Polytetrafluoroethylene (PTFE)) or custom hydrogels that have low flow resistance in the catheter lumen and high flow resistance in the walls (small pores) that assure a more even drug distribution. The use of multiple catheters as set forth in aspects of various embodiments of the present invention allows for the ability to customize the distribution of the drug to cover larger volumes of tissue. Additionally, the integration of microfluidic flow control assures for consistent flow to each of the catheters. Thus, the microporous catheters and multiple catheters under microfluidic control, as represented by various aspects of embodiments of the present invention, represents a significant departure from the conventional single catheter systems.

The present inventor also notes that current side by side catheters for the delivery of several drugs simultaneously having single end pores, is not viable because the drug distribution volumes will be unreasonably too limited, among other limitations.

Non-Limiting Illustrative Aspects of Embodiments

Referring to various aspects of embodiments represented by FIGS. 1-9, a distribution system 11 that is configured to allow individualized or customized flow control of infusate 23 to each of a plurality of branch catheters 41 to a selected site 1 of a subject 3 is provided.

FIG. 1 schematically illustrates an embodiment of the distribution system 11 to allow individualized or customized flow control of infusate 23 to each of a plurality of branch catheters 41 to a selected site 1 of a subject 3. The base catheter 31 may be configured for providing a passage for the infusate, supplied to the system, and the base catheter may include a supply end 33, a distal end 37, and an elongated body 38 there between. The plurality of branch catheters 41 may comprise a juncture end 43, a delivery end 47, and an elongated body 48 there between, wherein a portion the elongated body comprises a region having a microporous structure 51.

In an embodiment, the delivery ends provide an array 49 of the plurality of the branch catheters 41 wherein each of the plurality of the branch catheters 41, with their said microporous structure 51, are each configured to be independently inserted into the selected site 1 of the subject 3 to a specific inserted position, wherein said microporous structures 51 are configured to allow the infusate 23 to egress from said microporous structure 51 to the selected site 1.

Still referring to FIG. 1, a micro flow control device 61 may be provide in fluidic communication with each of said plurality of branch catheters 41; wherein said micro flow control device 61 is configured to control, for each of said plurality of branch catheters, flow rate and volume of the infusate egressing from said microporous structure 51 to the selected site 1 in the specified inserted position.

In an embodiment, the selected site 1 may be a tumor 5 or other target zone or target region of the brain 7 or other organ (or targeted anatomy).

In an embodiment, the infusate 23 may include any combination of the one or more of the following: therapeutic agent, diagnostic agent, or medication (or treatment material). In an embodiment, different types of infusate may flow within different individual plurality of branch catheters.

In an embodiment, the distribution system 11 may further comprise a controller 27. In an embodiment the controller 27 may include any combination of one or more of the following: microcontroller, processor, or microprocessor in communication with the micro flow control device 61 configured to control operation of said micro flow control device 61.

In an embodiment, the distribution system 11 may further comprise a reservoir 21 configured for containing a supply of the infusate 23, and wherein said supply end 33 of said base catheter 31 may be in fluidic communication with said reservoir 21 to allow for passage of the infusate 23 to pass through said base catheter 31. The reservoir 21 may be any container, tank, conduit, receptacle or the like so as to provide the supply of infusate.

Figure 8:
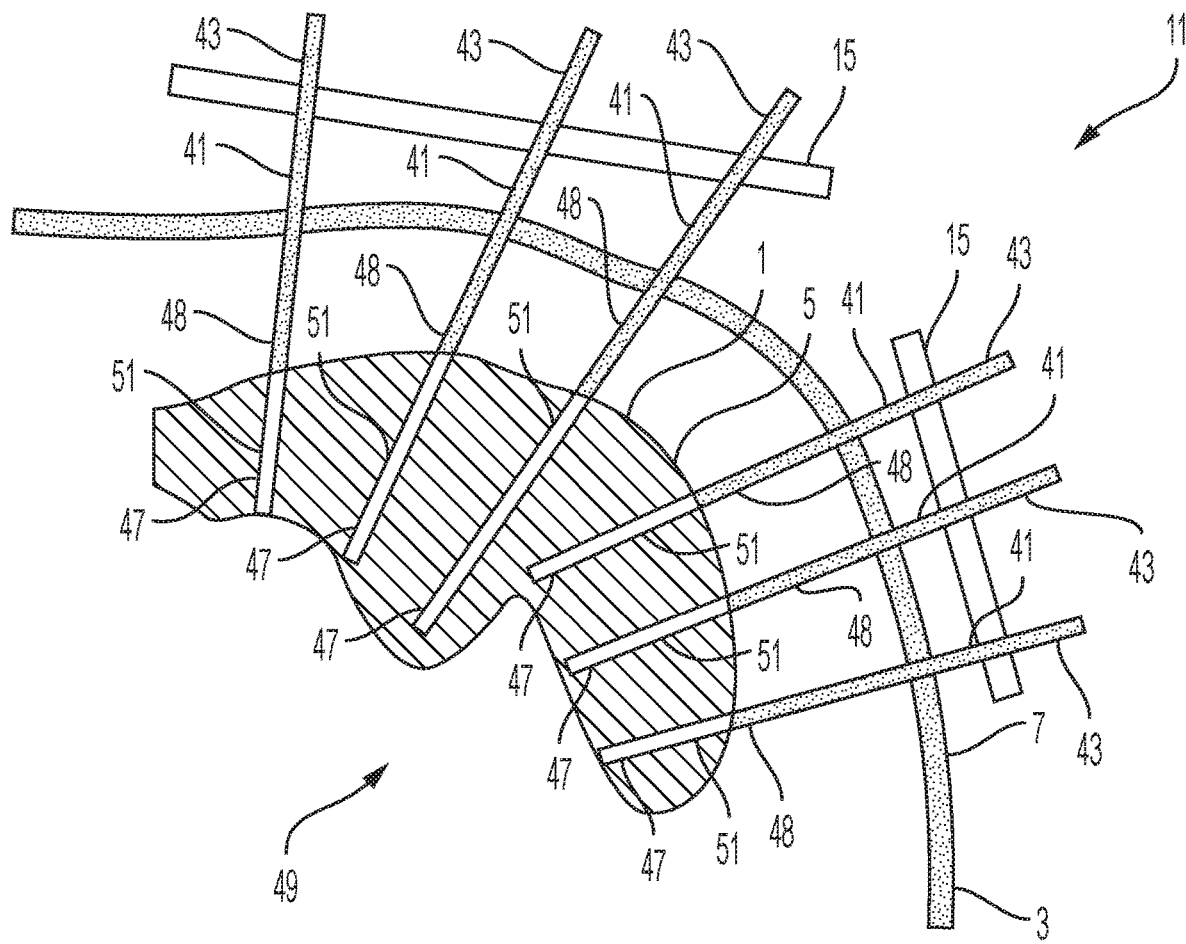
FIG. 8 schematically illustrates an embodiment of the distribution system to allow individualized or customized flow control of infusate to each of a plurality of branch catheters to a selected site of a subject A retainer device is configured to separate and hold each of the plurality of branch catheters and wherein the delivery ends provide an array of the plurality of the branch catheters, with their microporous structure, are held by the retainer device and separated from one another by the retainer device while being inserted into the selected site of the subject to a specific inserted position. And wherein the microporous structures are configured to allow the infusate to egress from the microporous structure to the selected site.

In an embodiment, the distribution system 11 may further include a retainer device 15 (as shown, for example, in FIG. 8, configured to separate and hold each of said plurality of branch catheters 31. Accordingly, an embodiment that includes a retainer device 15 may thereby include the delivery ends 47 to provide an array 49 of the plurality of the branch catheters 41 whereby each of the plurality of the branch catheters, with their microporous structure, are held by the retainer device 15 and separated from one another by said retainer device 15 while being inserted into the selected site 1 of the subject 3 to a specific inserted position, and wherein said microporous structures 51 are configured to allow the infusate 23 to egress from said microporous structure 51 to the selected site 1.

In an embodiment, the retainer device 15 may be in contact with said plurality of branch catheters 41 at the delivery end 47 of the plurality of branch catheters 41 or other location as desired or required.

In an embodiment, the retainer device 15 may be in contact with said plurality of branch catheters 41 at the elongated body 48 of said plurality of branch catheters 41 or other location as desired or required.

In an embodiment, the retainer device 15 may include at least one or more of any combination of the following: clamp, holder, lock, coupling, clasp, bracket, press, or vice.

The retainer device 15 may have opposing parts or segments that may be brought together for holding or compressing the branch catheters. The retainer device 15 may be configured for bracing, holding, clenching, and securing. The retainer device may be a substrate or plane having apertures or slots therein to allow for passage of the branch catheters through the apertures or slots for retention and separation.

Figure 2:
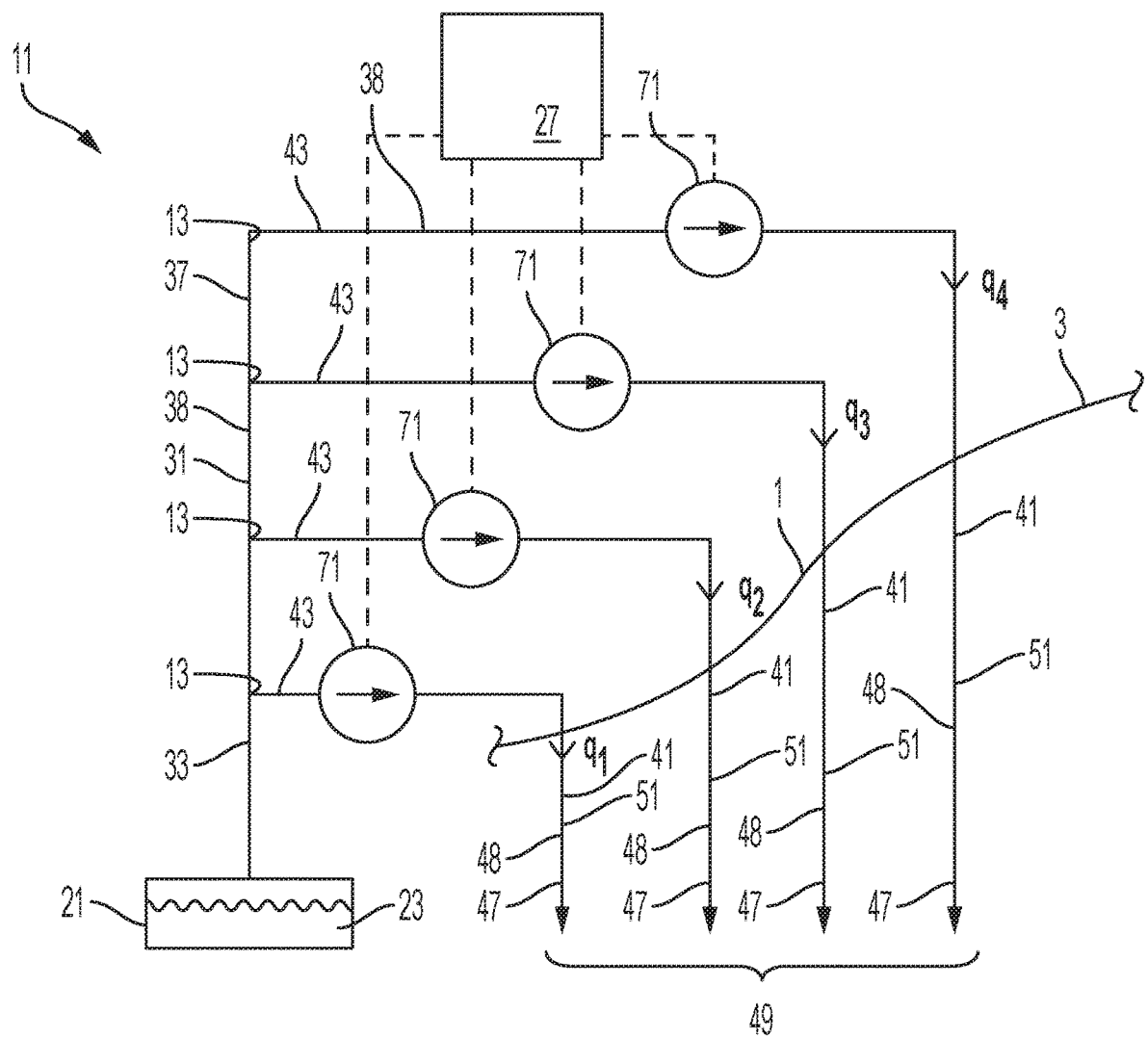
FIG. 2 schematically illustrates an embodiment of the distribution system to allow individualized or customized flow control of infusate to each of a plurality of branch catheters to a selected site of a subject; and wherein at least one of a plurality of pumps may be disposed on at least one of the plurality of branch catheters.

FIG. 2 schematically illustrates an embodiment of the distribution system 11 to allow individualized or customized flow control of infusate 23 to each of a plurality of branch catheters 41 to a selected site 1 of a subject 3; and wherein the micro flow control device 61 may comprise a plurality of pumps 71, wherein at least one of a plurality of pumps 71 is disposed on at least one of said plurality of branch catheters. In an embodiment, the pump 71 may be a micro pump or other device (or the like) for moving or compressing a solid, liquid or gas.

In an embodiment, the micro flow control device 61 may comprises a flow sensor 81 (not shown in FIG. 2), wherein said flow sensor 81 may be disposed in fluidic communication on said base catheter 31. In an embodiment, the micro flow control device 61 may comprises a plurality of flow sensors 81 (not shown in FIG. 2), wherein at least one of said plurality of flow sensors 81 may be disposed in fluidic communication on said base catheter 31.

FIG. 13 schematically illustrates an embodiment of the distribution system 11 to allow individualized or customized flow control of infusate 23 to each of a plurality of branch catheters 41 to a selected site 1 of a subject 3; and wherein the micro flow control device may comprise a plurality of pumps 71, wherein at least one of a plurality of pumps 71 is disposed on at least one of said plurality of branch catheters 41. In an embodiment, the pump 71 may be a micro pump or other device (or the like) for moving or compressing a solid, liquid or gas. Further, wherein the micro flow control device may comprise a plurality of flow sensors 81, wherein at least one of a plurality of flow sensors 81 is disposed on at least one of said plurality of branch catheters 41.

Figure 3:
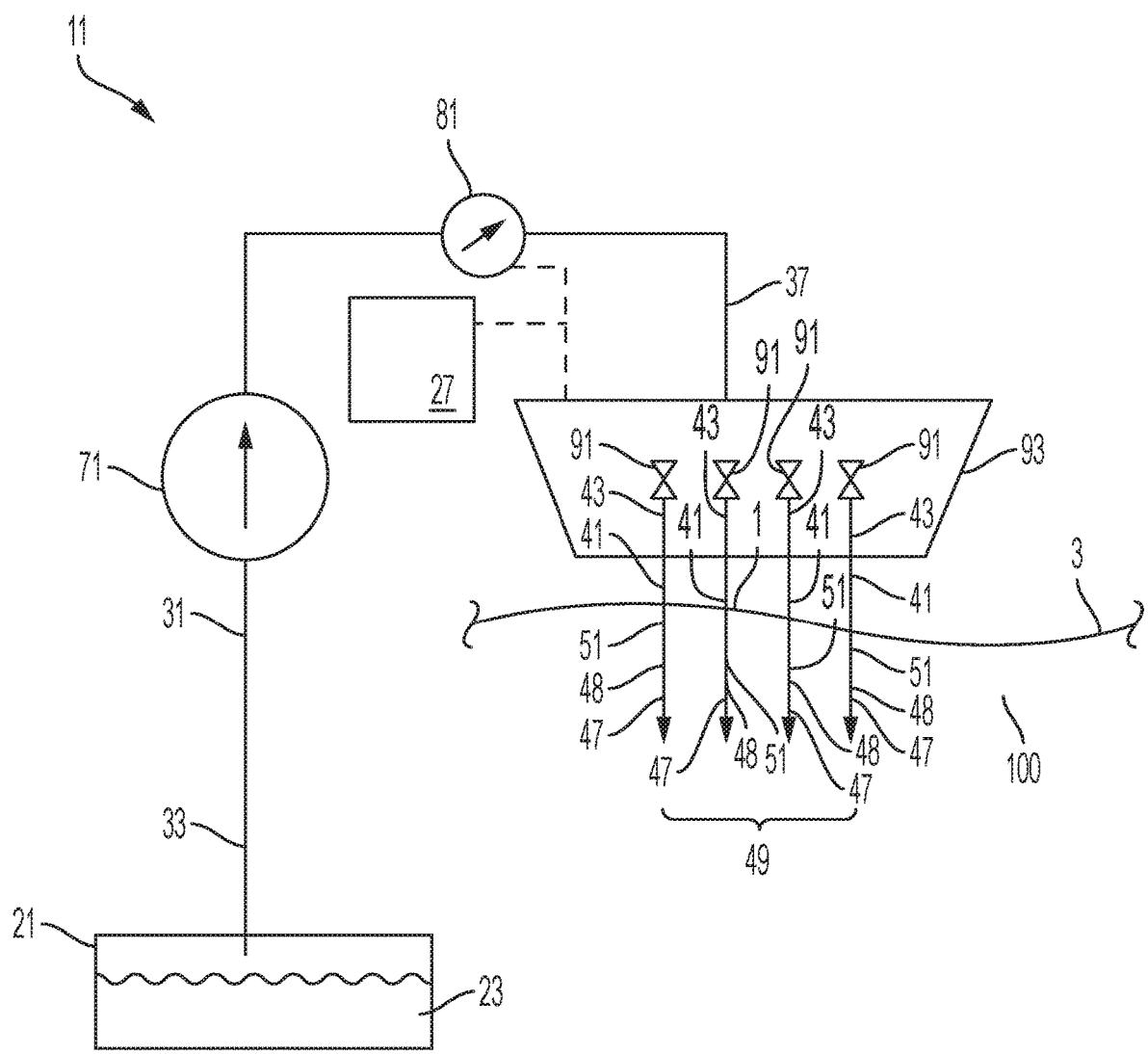
FIG. 3 schematically illustrates an embodiment of the distribution system to allow individualized or customized flow control of infusate to each of a plurality of branch catheters to a selected site of a subject; and wherein at least one of plurality of branch catheter valves may be disposed on at least one of the plurality of branch catheters.

FIG. 3 schematically illustrates an embodiment of the distribution system 11 to allow individualized or customized flow control of infusate 23 to each of a plurality of branch catheters 41 to a selected site 1 of a subject 3; and the micro flow control device 61 may comprise a plurality of branch catheter valves 91, wherein at least one of plurality of branch catheter valves 91 is disposed on at least one of said plurality of branch catheters 41. In an embodiment, said plurality of branch catheter valves 91 is collectively configured as a flow multiplexer (MUX). In an embodiment, and the micro flow control device 61 may comprise a flow sensor 81, wherein said flow sensor 81 may be disposed in fluidic communication on said base catheter 31. In an embodiment, the distribution system 11 may further comprising a pump 71, wherein said pump 71 is disposed in fluidic communication on said base catheter 31.

In an embodiment, the micro flow control device 71 may further comprises a plurality of flow sensors 81 (not shown in FIG. 3), wherein at least one of said plurality of said flow sensors 81 is disposed in fluidic communication on said plurality of branch catheters 41. In an embodiment, the distribution system 11 may further comprising a plurality of pumps 71, rather than a single pump, wherein at least one of the plurality of said pumps 71 is disposed in fluidic communication on said plurality of branch catheters 41.

Figure 4:
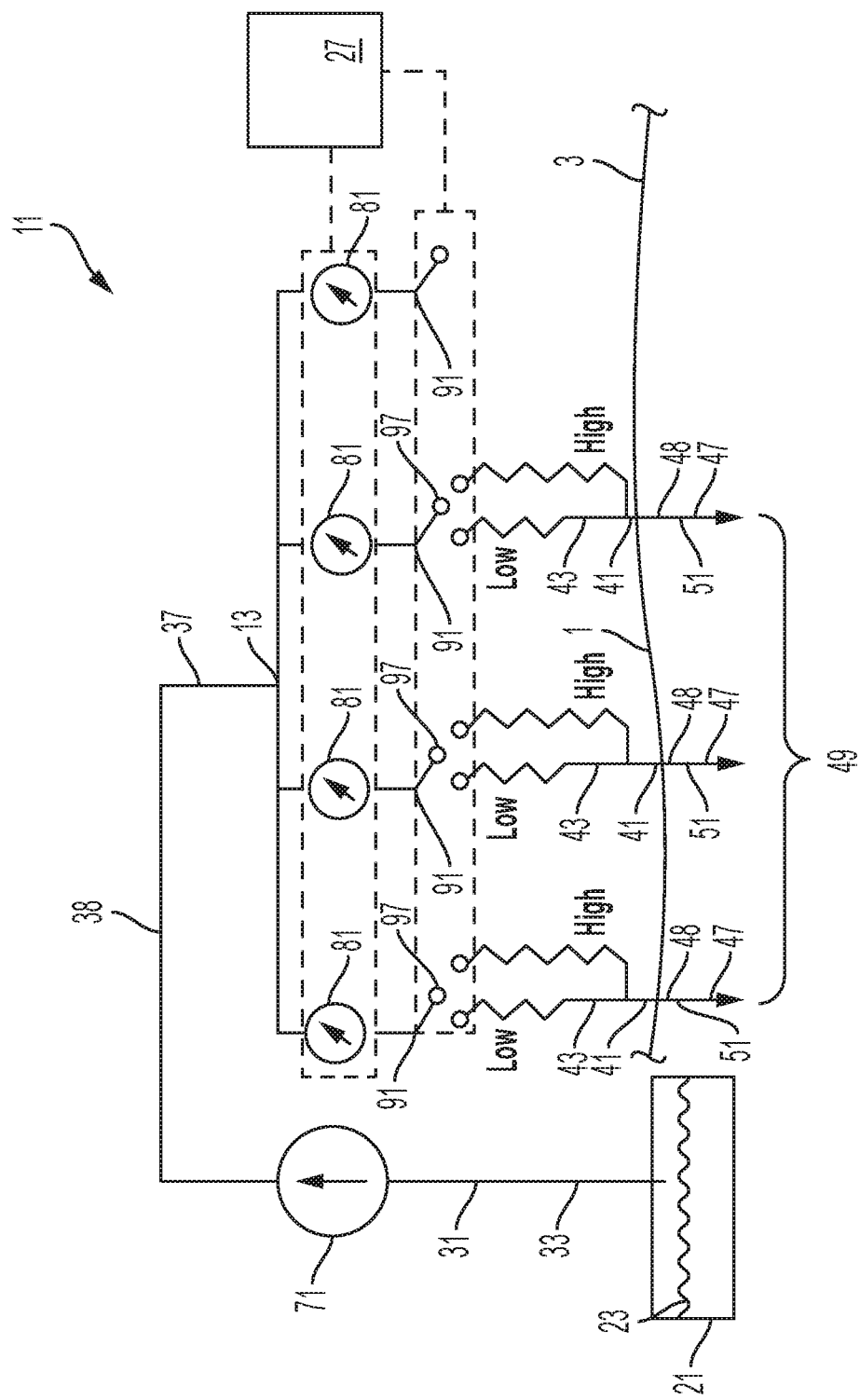
FIG. 4 schematically illustrates an embodiment of the distribution system to allow individualized or customized flow control of infusate to each of a plurality of branch catheters to a selected site of a subject; and wherein at least one of a plurality of flow sensors is disposed on one or more of the plurality of branch catheters. At least one of a plurality of branch catheter valves is disposed on at least one of the plurality of branch catheters; and wherein the plurality of valves comprises at least one switch, wherein at least one switch is configured to adjust flow rate and/or volume of infusate through the branch catheter.

FIG. 4 schematically illustrates an embodiment of the distribution system 11 to allow individualized or customized flow control of infusate 23 to each of a plurality of branch catheters 41 to a selected site 1 of a subject 3; and wherein the micro flow control device 61 may comprise at least one of a plurality of flow sensors 81 that may be disposed on one or more of said plurality of branch catheters 41 and wherein at least one of plurality of branch catheter valves (91) may be disposed on at least one of said plurality of branch catheters 41. The plurality of valves 91 may comprises at least one switch (97), wherein said at least one switch 97 is configured to adjust flow rate and/or volume of infusate 23 through said branch catheter 41. In an embodiment, the distribution system 11 may further comprise a pump 71, wherein said pump 71 may be disposed in fluidic communication on said base catheter 31 (or alternatively in communication on the branch catheters 41).

In an embodiment, the system may further comprise a plurality of pumps 71 (rather than a single pump), wherein at least one of said plurality of pumps 71 is disposed on at least one of said plurality of branch catheters 41.

Figure 5:
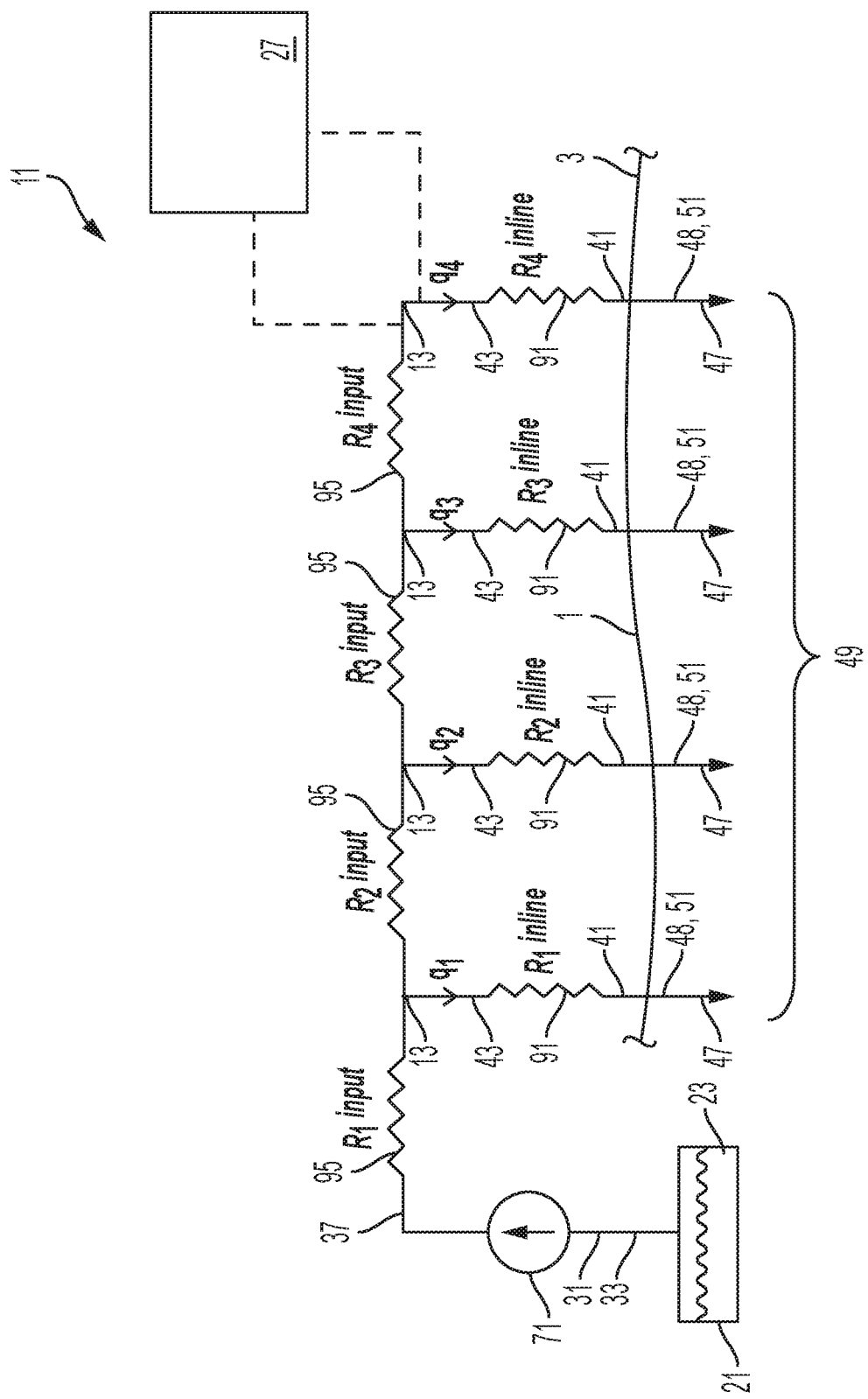
FIG. 5 schematically illustrates an embodiment of the distribution system to allow individualized or customized flow control of infusate to each of a plurality of branch catheters to a selected site of a subject; and wherein at least one of a plurality of base catheter valves is disposed on a base catheter and at least one of plurality of branch catheter valves is disposed on at least one of the plurality of branch catheters.

FIG. 5 schematically illustrates an embodiment of the distribution system 11 to allow individualized or customized flow control of infusate 23 to each of a plurality of branch catheters 41 to a selected site 1 of a subject 3; and wherein the micro flow control device 61 may comprise at least one of said plurality of base catheter valves 95 that may be disposed on said base catheter 31 wherein at least one of plurality of branch catheter valves (91) is disposed on at least one of said plurality of branch catheters 41. In an embodiment, the plurality of branch catheters 41 intercept said base catheter 31, wherein said interception provides one or more junctures 13 to provide fluidic passage between said base catheter 31 and said plurality of branch catheters 41. In an embodiment, at least one of said plurality of base catheter valves 95 is located adjacent to at least one or more of said junctures 13 opposite from said branch catheter 41. In an embodiment, at least one of said plurality of branch catheter valves 91 is located adjacent to at least one or more of said junctures 13 opposite from said base catheter 31.

Figure 6:
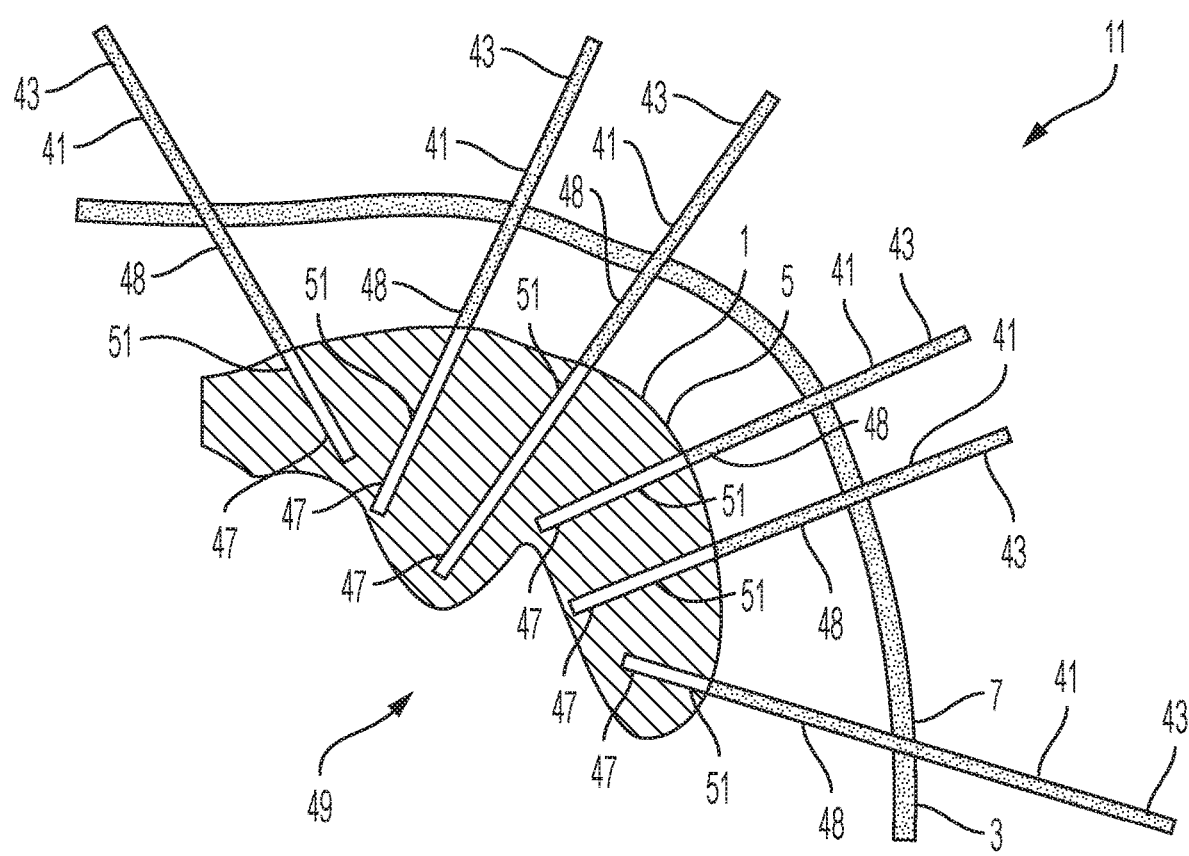
FIGS. 6 and 7 schematically illustrates an embodiment of the distribution system to allow individualized or customized flow control of infusate to each of a plurality of branch catheters to a selected site of a subject; and wherein an array of the plurality of the branch catheters, with their microporous structure, are each configured to be independently inserted into the selected site of the subject to a specific inserted position, wherein the microporous structures are configured to allow the infusate to egress from the microporous structure to the selected site.
Figure 7:
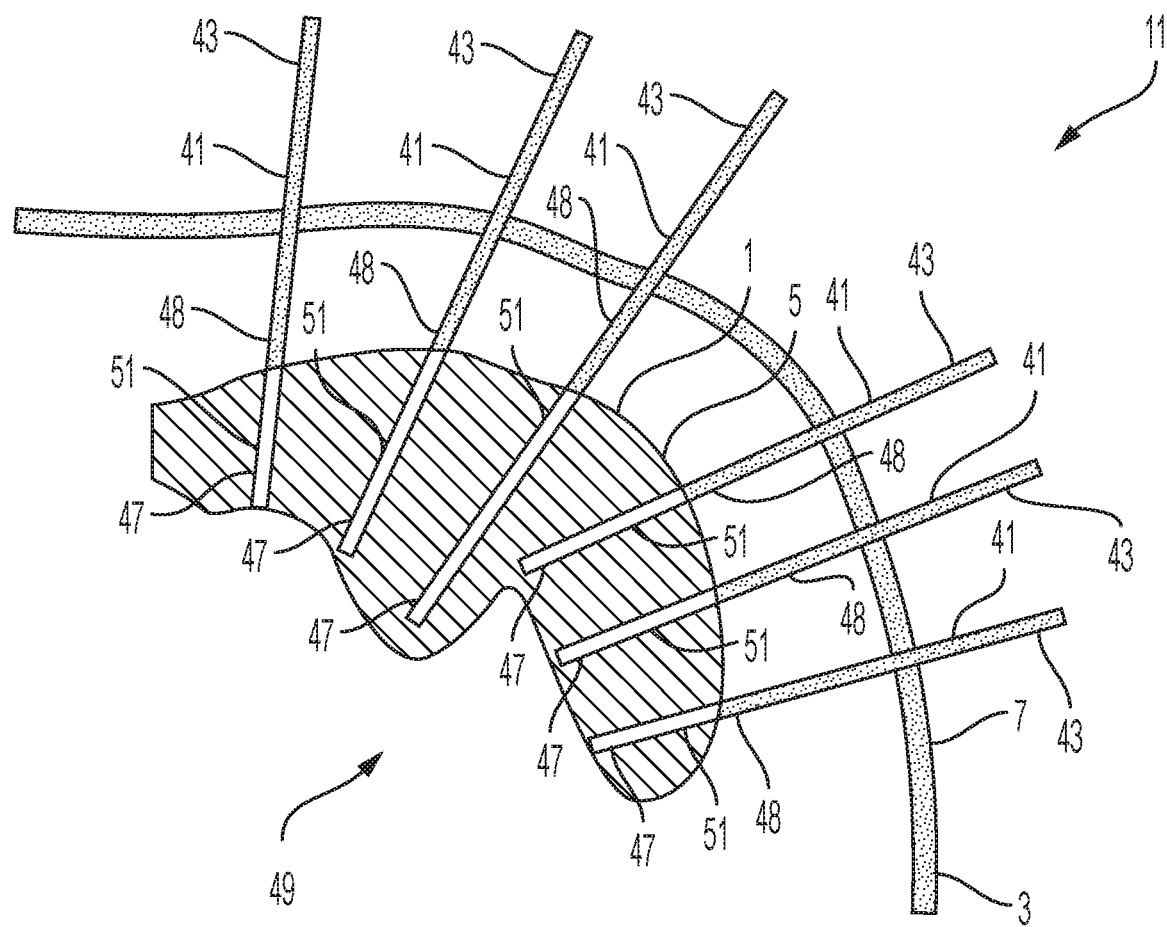

FIGS. 6 and 7 schematically illustrates an embodiment of the distribution system 11 to allow individualized or customized flow control of infusate 23 to each of a plurality of branch catheters 41 to a selected site 1 of a subject 3; and wherein an array 49 of said plurality of said branch catheters 41. The plurality of said branch catheters, with their microporous structure 51, are each configured to be independently inserted into the selected site 1 of the subject 3 to a specific inserted position, wherein said microporous structures 51 are configured to allow the infusate 23 to egress from said microporous structure 51 to the selected site 1. In an embodiment, for example, the selected site 1 may be a tumor 5 (or tumors) or other target zone(s) or target region(s) of the brain 7.

FIG. 8 schematically illustrates an embodiment of the distribution system 11 to allow individualized or customized flow control of infusate 23 to each of a plurality of branch catheters 41 to a selected site 1 of a subject 3; and wherein a retainer device 15 may be configured to separate and hold each of said plurality of branch catheters 41 and wherein said delivery ends provide an array 49 of said plurality of said branch catheters 41. The plurality of said branch catheters 41, with their said microporous structure 51, are held by said retainer device and separated from one another by said retainer device 15 while being inserted into the selected site 1 of the subject 3 to a specific inserted position, wherein said microporous structures 51 are configured to allow the infusate 23 to egress from said microporous structure 51 to the selected site 1.

Figure 9:
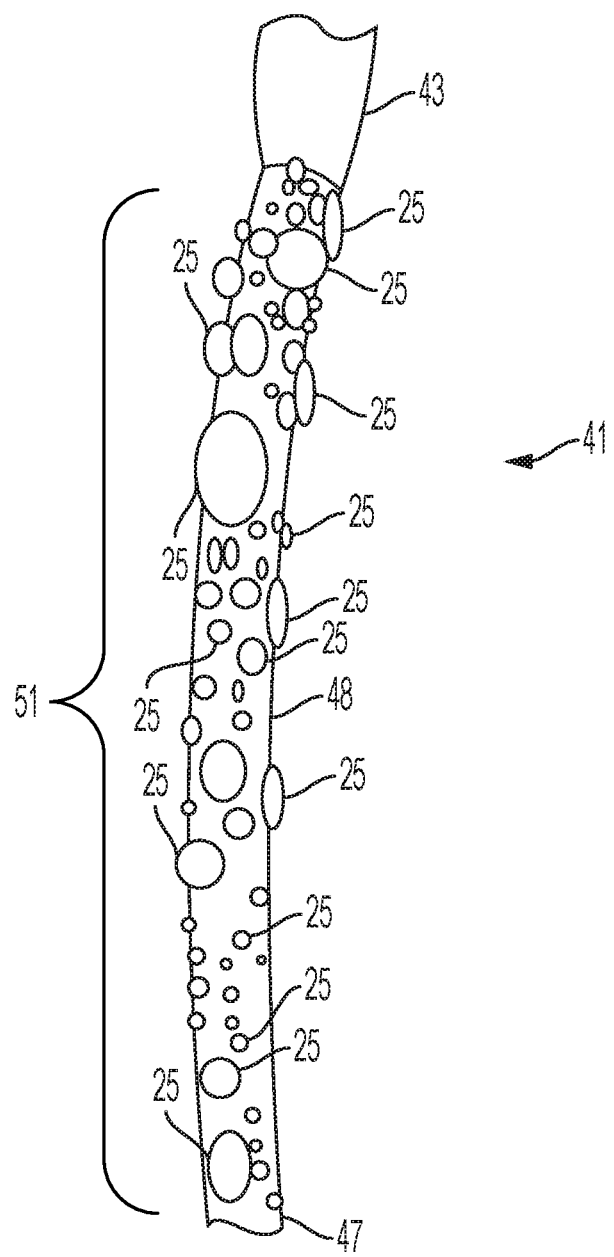
FIG. 9 schematically illustrates an enlarged partial view of a branch catheter having droplets 25 of infusate (as represented by dye in experiment) egressing from its microporous structure on the body of the branch catheter.

FIG. 9 schematically illustrates an enlarged partial view of a branch catheter having droplets 25 of infusate (as represented by dye in the present inventor's experiment) egressing from its microporous structure 51 on the body 48 of the branch catheter 41.

In an alternate embodiment and not shown, an aperture or apertures could be disposed on the distal tip of the branch catheter in addition to microporous structure on the side wall of branch catheter body (or instead of the microporous structure on the side wall of the branch catheter body).

EXAMPLES

Practice of an aspect of an embodiment (or embodiments) of the invention will be still more fully understood from the following examples and experimental results, which are presented herein for illustration only and should not be construed as limiting the invention in any way.
Example and Experimental Results Set No. 1

In this project the present inventor will determine the most effective approach to microfluidic control. One embodiment is a single pump 71 connected to a multiplexer 93 (for example, but not limited thereto, generally reflected in FIG. 3) that switches across the catheters 41 in sequence. A second embodiment is a micropump for the pump 71 for each catheter 41 that delivers an individualized low volume flow to each catheter 41 (for example, but not limited thereto, generally reflected FIG. 2). There are two specific aims by the experiment of the present inventor, among others:

1. Demonstrate that a single pump multiplexed delivery system (e.g., FIG. 3) has the same consistent delivery as individual micropumps to each catheter (e.g., FIG. 2). The present inventors will determine whether switching across the catheters from a single pump has the same performance as supplying each catheter with individual micropumps in delivering consistent volumes over 24 hour periods.

2. Determine that infusion distribution in gels predicts in vivo distribution. Gels are uniform materials that are mostly aqueous and are convenient for determining diffusion patterns from a catheter. The brain is a different environment with many hydrophobic fibers running in different directions so that diffusion may be very different. If there are differences, modeling for use in vivo will need to take the differences into consideration. In this aim the present inventor will compare distribution of gadolinium in gels to distribution in the brains of anesthetized rodents.

Successful completion of the project shall revolutionize the treatment of brain tumors, by direct drug delivery to the tumor instead of through blood vessels that prevent drugs from crossing the blood brain barrier. The project will provide the key data for the development of a multiple catheter delivery system and related method.

Significance and potential impact. There are an estimated 25,000 people in the United States diagnosed with essentially untreatable malignant brain tumors every year. Current treatment by intravascular infusion is limited by the blood brain barrier which prevents most tumor drugs from entering the brain from the blood stream. The present inventor submits that the benefit of direct drug infusion has been generally limited. The present inventor submits that direct acute infusion into human brain tumors are ineffective when the catheters were centered into certain tumors or larger tumors. Currently, most tumors are too large to achieve a therapeutic concentration throughout (See Sampson et al., 2008; and Sewing et al., 2017). Attempts to overcome these issues with higher rates of delivery (convection enhanced delivery) are limited by, among other things, the reflux along the catheter path when the rate of infusion exceeds the brain's capacity to absorb the infusate from the single point of infusion (See Heiss et al., 2005; Iyer et al., 2011; and Lewis et al., 2016).

An aspect of an embodiment of the present invention includes, among other things, microporous catheters that provide a more even distribution of infusate along each catheter length and a microfluidic control system that will deliver precise volumes to each catheter. This design makes drug delivery patterns scalable in all three dimensions. An aspect of an embodiment of the present invention provides, among other things, the microfluidic control systems along with testing the system in animals to confirm similar patterns in vivo as well as initial efforts to demonstrate efficacy in an animal model of gliomas.

Research Plan. One of the goals of this project, among others, is to determine if a multiplexed single pump control system (e.g., FIG. 3) has the same delivery through an array of the microporous catheters as a system with dedicated micropumps for each catheter (e.g., FIG. 2). One of the points for comparison will be volume of infusate delivered from each catheter and the consistency of distribution with each control system. Multiplexed control may be easier to bring to the clinic as there are several implantable infusion pumps in existence to which multiplexed catheters could be attached.

Test system components. One of the basic design embodiments for testing will include a reservoir for the infusate and a pump or pumps that will deliver to multiple catheters. For the multiple micropump system (e.g., FIG. 2), each pump will be connected to the reservoir and then individually to a single catheter in the array. For the multiplexer system (e.g., FIG. 3), there will be a single pump connected to the reservoir on one end and to the multiplexer distributor on the output side. The output from the microfluidic multiplexer will go to individual catheters.

FIG. 9 provides a depiction illustrating even distribution of dye droplets (representing the infusate droplets) around the catheter 41, such as for example, active zone of the PTFE microporous catheter.

Referring to the various embodiments of disclosed herein, the egress of infusate can be restricted to a customized length of the catheter.

A focus of this project, for example, is to determine if the two varying control systems have equivalent delivery performance.

Figure 10A:
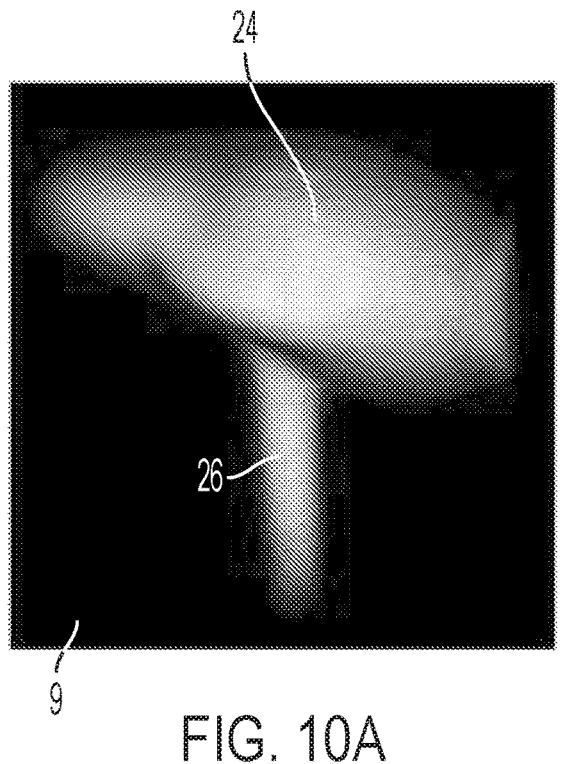
FIG. 10 represents 3D reconstruction of a magnetic resonance image (MRIs) of gadolinium infusion 24 into gel 9 (gelatin phantom) with the same delivered volume of which an image from a single catheter with an opening at the tip that is provided in FIG. 10A as well as an image from a two microporous catheters that is provided FIG. 10B.
Figure 10B:
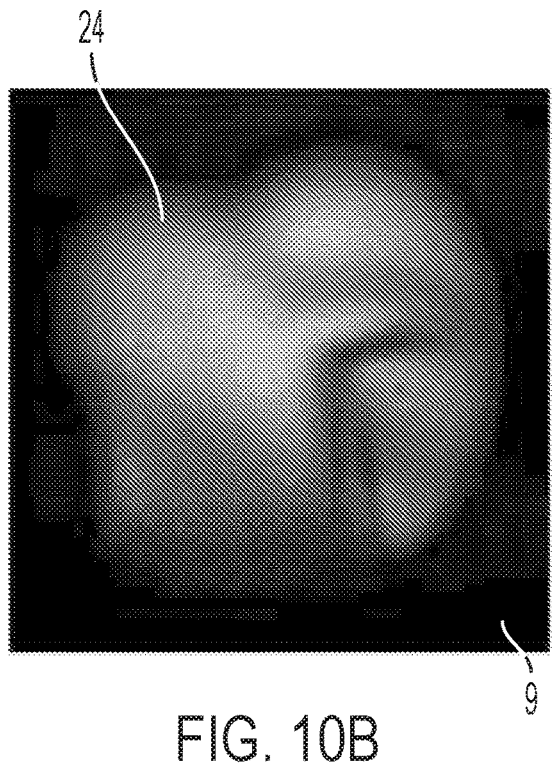

FIG. 10 represents 3D reconstructions of MRIs of gadolinium infusion 24 into a gel 9 (gelatin phantom) with the same delivered volume (0.7 ml). The image of FIG. 10A is from a single catheter with an opening at the tip and the image of FIG. 10B is from two microporous catheters which delivered a much more even concentration over a larger volume. There was reflux 26 along the insertion track of the single standard catheter (i.e., of FIG. 10A) with about 20% of delivered volume from the single catheter refluxed to the surface of the gel 9. Thus, the multiple microporous catheter approach (i.e., of FIG. 10B) may improve the focal delivery of therapies.

FIGS. 2 and 3 provides a schematic illustration of a design of an embodiment of one of the proposed delivery systems. FIG. 2 is the multiple micropump system, with each pump delivering directly to single catheter. FIG. 3 is the microfluidic multiplexed valve system with a single pump connected to a valve that delivers to each catheter that may be in a rotating sequence.

Figure 11A:
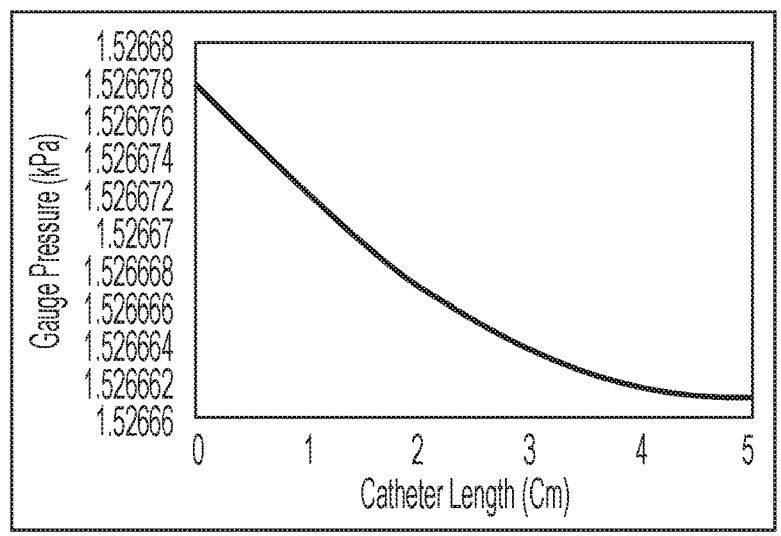
FIGS. 11A and 11B graphically illustrates some of the calculations for pressures at different points along the catheter and FIG. 11C graphically illustrates estimates of pore flow along the 5 cm of the catheter in microliters/minute per pore.
Figure 11B:
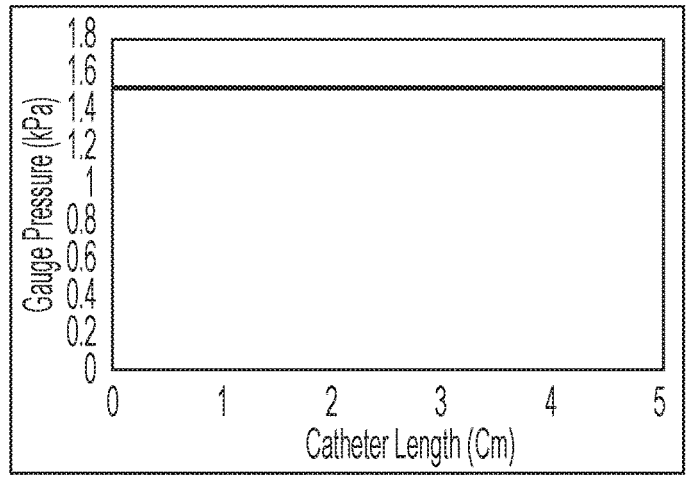
Figure 11C:
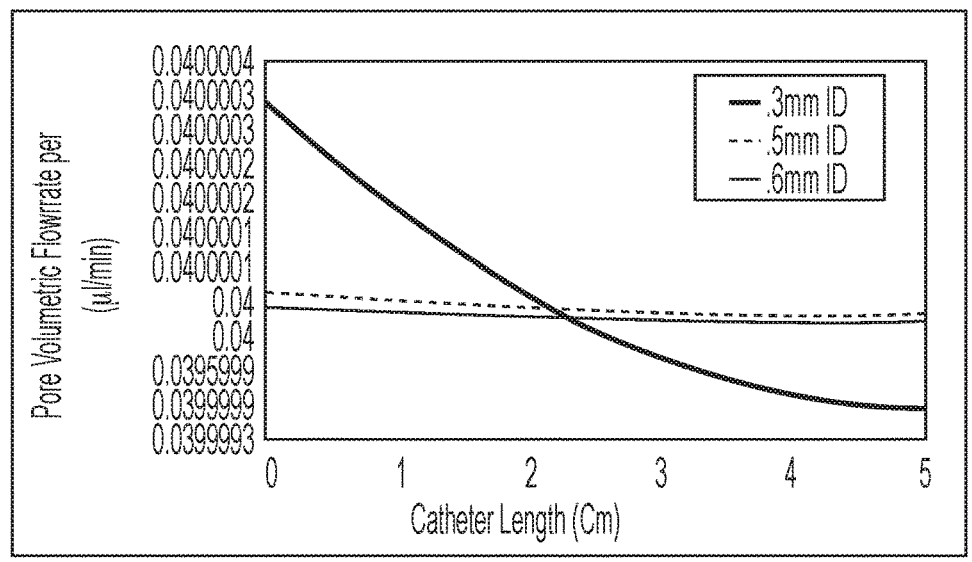

FIG. 11 graphically illustrates some of the calculations for pressures at different points along the catheter. FIGS. 11A and 11B graphically show the same estimated gauge pressures along the length of the catheter (0 to 5 cm) with an inner diameter of 0.3 mm in different vertical scales of kilopascals (kPa) with pore diameter and density as outlined in the disclosure. The graph of FIG. 11A shows that the pressure fall over 5 cm is a negligible 0.000012 kPa. The graph of FIG. 11B shows the same data in a larger scale to emphasize that the pressure drop is negligible. The graph of FIG. 11C shows estimates of pore flow along the 5 cm of the catheter in microliters/minute per pore. Inner diameters more than 0.5 mm do not alter pore flow over the 5 cm. The modeling was performed using the Hagen-Poiseuille equation for hydrodynamic circuit function for flowrate and pressure differentials based on our tubing geometries and an input flowrate of 8 μl/minute.

Micropumps. Micro-pumps are commercially available and can provide exact flow rates to each catheter (e.g., Laser and Santiago, 2004; Brian et al. 2008) and they have flow rates as low as a few microliters per minute, fitting our requirements (FIG. 2, for example). Micropumps, among other features disclosed herein, enable the delivery of customized volumes.

Microporous tubing. An embodiment, for example, may utilize microporous tubing from ZEUS, Inc. The tubing can be further manufactured by the present inventors to custom specifications for porosity, diameter and wall thickness to achieve optimal patterns of distribution. In an embodiment, external diameter will be approximately 2 mm to minimize insertion damage but have sufficient substance for insertion and manipulation. In an embodiment, the design specifications of 0.9 mm inner diameter results in negligible pressure drops along the catheter length.

Microfluidic flow switch multiplexers. In an embodiment, precision delivery to each catheter is rotated using an inline flow sensor. For example, a flow sensor 81 is generally shown in FIG. 4. An aspect of an embodiment of the present invention provides, among other things, for example, two designs: a) a flow multiplexer (MUX) (for example a MUX 93 is generally shown in FIG. 3) for sequentially selecting each path or b) a piezoelectric flow switch between "High" to "Low" resistance paths. For example, switches 97 are generally shown in FIG. 4, as well as the "High" and "Low" resistance paths. The former may be less challenging to construct, but can allow clogs to build-up during the "OFF" cycle. The latter is rapid with available of piezoelectric flow switches and flow measurement methods (See Brenner et al., 2005, for example). Clinical infusion pumps (For example, Medtronics and Flowonix) have adjustable infusion rates from 2 μl/hour to 1 ml/hour, a range that will fit the MUX and catheter performance requirements.

Referring to FIG. 5, for example, dynamic balancing of flow resistances may be implemented. In a first approach, the present inventor will explore flow rate control through dynamic balancing of flow resistances at branch points, as per FIG. 5. In an embodiment, the system my control the flow rate through each of the catheters by controlling the respective input and inline resistances.

The length of tubing will be used to add or remove flow resistances at each node to alter the flow rate (q). These resistance (R) values can be computed using Kirchhoff's current law, based on an electrical analogy. For instance, if a constant flow rate is of interest: i.e. $q_1=q_2=q_3=q_4$; then we can choose the input resistances to be:

$R_{1,2,3,4}^{input}=10\ \Omega$;

while varying the inline resistances as follows:
$R_1^{inline}=160\ \Omega$;
$R_2^{inline}=130\ \Omega$;
$R_1^{inline}=110\Omega$; and
$R_1^{inline}=100\ \Omega$.

This will give a constant current (analogous to flow) of 2 Amps (A) at each node. In this design, even if the first catheter were clogged, the flow rate would increase to a constant value for the other following catheters.

Figure 12:
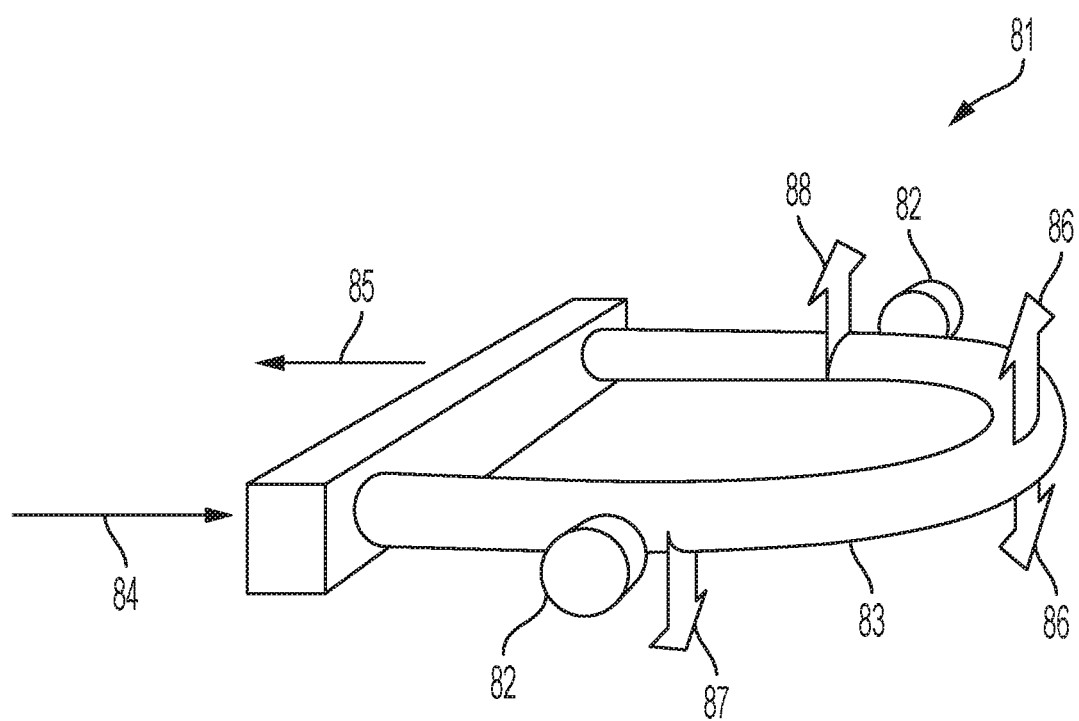
FIG. 12 schematically illustrates an embodiment of a particular type of a flow sensor device.

As discussed above, FIG. 4 includes a plurality of flow sensors 81; of which may be a variety of types of flow sensors as desired or required. FIG. 12 schematically illustrates a particular type of a flow sensor being a miniaturized Coriolis microfluidic flow sensor; of which is provided so as to include an optical measurement component 82.

The flow sensor components of both the designs utilizing the MUX (for example, FIG. 3) and piezo electric switches (for example, FIG. 4) may be used as inline monitors of the volumetric flow rate delivered to each of the catheters. They may be included to monitor any changes in volumetric flow rate over the course of drug delivery, to not only provide accurate dosage values, but also to detect any substantial change in flow rate, which may indicate a leak or clog in the system, for example. Other versions of such in line volumetric or mass flow sensors may be utilized, for example, of which one type of a flow sensor may utilize the Coriolis Principle. As shown in FIG. 12, for example, these mass flow sensors 81 may contain a bent tube 83 which is vibrated at a constant rate by an exciter. As fluid flows through this excited tubing 83 its inertia will cause a phase shift in the vibration (i.e., twisting) before and after the point of excitation. Optical measurements of this phase shift (as shown by component 82) may be used to measure mass or volumetric flow through the tubing.

The component 82 is used to measure the phase shift (i.e. twisting or vibration) of the vibrating tube 83 caused by the inertia of the flowing material. This phase shift may be used to measure the mass and volumetric flow. The flow in arrow 84 and flow out arrow 85 are indicating the inlet, outlet, and direction of fluid flow in the system. The remaining large arrows are indicating the vibration of the tubing 83, with arrow, 86, farthest to the right of the figure indicating the point of excitation, and the other two arrows, 87 and 88, indicating the phase shifted vibration at the point of measurement.

Moreover, in an embodiment, other integrated versions utilizing a similar design may be implemented.

Aim 1. Determine if the single pump multiplexed system (e.g., FIG. 3) delivers the same volumes through the catheters as the multiple micropumps (e.g., FIG. 2). In an embodiment of a multiple catheter array each catheter may receive a consistent volume. The first comparison is volume delivered by each catheter. The two systems will be set to deliver the same volume to each catheter in the array over 24 hours. Consistent volumes over different flow rates will be the primary comparison, and less than 10% variance from the mean will be the standard measure. Secondly to compare consistency in distribution from each catheter, gadolinium solutions will be infused through the microporous catheters into gels, and the gels will be scanned in the small animal MRI for the distribution around each catheter. This approach provides an image of infusion distribution at a set moment in time. Distributions will be compared by how close each infusion comes to creating an ideal cylinder along the active zone of the catheter, with the standard being less than 10% variation in the diameter of distribution at predetermined points on the length of the catheter and with little extension above and below the active zone at the ends of the catheter. Variation will be detected if there is a consistent change in diameter along the length.

Aim 2. Determine that in vivo distribution is predicted by distribution in gels. Gels offer a uniform protein/water matrix for that provides a standardized environment for diffusion, but they are a very different environment than the brain which is a network of fibers and cell matrices, which may redirect flow less uniformly. In this aim the present inventor will compare the distribution patterns of infusion into gels with the pattern in the brain, with the same analysis of deviation from the ideal cylinder. After predetermined volumes of gadolinium are delivered stereotactically to anesthetized rats, the animals will be scanned for comparison to the distribution in gels.

Quantifying spatial distribution of infusate. One of the points for analysis is reproducible uniformity in distribution around the active zone (portion of catheter with pores) of the catheter. Images for distribution analysis in the gels and the animals will be obtained with the University's small animal 7T MRI scanner that will provide 3D volume sets that will facilitate spatial analysis with Osirix software which the investigators have. In addition to the measure of infusate diameter the present inventor will quantify gadolinium concentrations through a statistical description of particle distribution across the geometry (See Rohani et al. 2009), over the background level. The concentration of particles can then be computed by measured signal intensity from the images.

Analysis summary. The first level of analysis may be on the delivery of reproducible volumes across all catheters comparing the two control systems (multiplexer (e.g., FIG. 3) and multiple micropumps (e.g., FIG. 3)). The present inventor will then evaluate the pattern of gadolinium distribution in gels to determine which control system delivers a uniform distribution along the active zone as determined by comparison of infusate diameters at predetermined points along the catheter length. This analysis will confirm our modeling of catheter parameters for assuring uniform distribution. The final analysis will compare distributions in living brains of rodents to correlate gel predictions with in vivo performance in rodents (uniformity of cylinder diameter along the length of the catheter active zone). The present inventor are hypothesizing that the multiplexed control system will perform similarly to the multiple pump design. Developing a full clinical system will be facilitated by demonstration of equivalent performance across the two control systems because there are several existing implantable long term infusion systems that would interface well with a multiplexer (e.g., Medtronics Synchromed II and Flowonix Prometra). One of the novel aspects, among others, of the this project is the distribution and flow control to multiple catheters which will be key to the development of clinically useful systems for brain tumors as well as Alzheimer's, Parkinson's and epilepsy.

An aspect of an embodiment of the present invention method and system shall, among other things, provide a solution for direct infusion to the brain, and overcome the current limitations associated with infusion to the brain. An aspect of an embodiment of the present invention method and system for infusion shall, among other things, provide a technique for a therapeutic approach.

ADDITIONAL EXAMPLES

Example 1

A distribution system to allow individualized or customized flow control of infusate to each of a plurality of branch catheters to a selected site of a subject.

The distribution system may comprise:
a base catheter, configured for providing a passage for the infusate, supplied to the system, said base catheter includes a supply end, a distal end, and an elongated body there between;

said plurality of branch catheters comprise a juncture end, a delivery end, and an elongated body there between, wherein a portion of said elongated body comprises a region having a microporous structure;

wherein said delivery ends provide an array of said plurality of said branch catheters wherein each of said plurality of said branch catheters, with their said microporous structure, are each configured to be independently inserted into the selected site of the subject to a specific inserted position, wherein said microporous structures are configured to allow the infusate to egress from said microporous structure to the selected site; and a micro flow control device in fluidic communication with each of said plurality of branch catheters; wherein said micro flow control device is configured to control, for each of said plurality of branch catheters, flow rate and volume of the infusate egressing from said microporous structure to the selected site in the specified inserted position.

Example 2

The system of example 1, further comprising a controller, microcontroller, processor, or microprocessor in communication with said micro flow control device configured to control operation of said micro flow control device.

Example 3

The system of example 1 (as well as subject matter in whole or in part of example 2), further comprising a reservoir configured for containing a supply of the infusate, and wherein said supply end of said base catheter is in fluidic communication with said reservoir to allow for passage of the infusate to pass through said base catheter.

Example 4

The system of example 1 (as well as subject matter of one or more of any combination of examples 2-3, in whole or in part), wherein said micro flow control device comprises:
a plurality of pumps, wherein at least one of said plurality of pumps is disposed on at least one of said plurality of branch catheters.

Example 5

The system of example 4 (as well as subject matter of one or more of any combination of examples 2-4, in whole or in part), wherein at least one or more of said plurality of pumps is a micro pump Example 6

The system of example 4 (as well as subject matter of one or more of any combination of examples 2-3 and 5, in whole or in part), wherein said micro flow control device further comprises a flow sensor, wherein said flow sensor is disposed in fluidic communication on said base catheter.

Example 7

The system of example 4 (as well as subject matter of one or more of any combination of examples 2-3 and 5-6, in whole or in part), wherein said micro flow control device comprises further comprises a plurality of flow sensors, wherein at least one of said plurality of said flow sensors is disposed in fluidic communication on said plurality of branch catheters.

Example 8

The system of example 1 (as well as subject matter of one or more of any combination of examples 2-7, in whole or in part), wherein said micro flow control device comprises: a plurality of branch catheter valves, wherein at least one of said plurality of branch catheter valves is disposed on at least one of said plurality of branch catheters.

Example 9

The system of example 8 (as well as subject matter of one or more of any combination of examples 2-7, in whole or in part), wherein said plurality of branch catheter valves is collectively configured as a flow multiplexer (MUX).

Example 10

The system of example 8 (as well as subject matter of one or more of any combination of examples 2-7 and 9, in whole or in part), wherein said micro flow control device further comprises a flow sensor, wherein said flow sensor is disposed in fluidic communication on said base catheter.

Example 11

The system of example 10 (as well as subject matter of one or more of any combination of examples 2-9, in whole or in part), further comprising a pump, wherein said pump is disposed in fluidic communication on said base catheter.

Example 12

The system of example 8 (as well as subject matter of one or more of any combination of examples 2-7 and 9-11, in whole or in part), wherein said micro flow control device further comprises a plurality of flow sensors, wherein at least one of said plurality of said flow sensors is disposed in fluidic communication on said plurality of branch catheters.

Example 13

The system of example 12 (as well as subject matter of one or more of any combination of examples 2-11, in whole or in part), further comprising a plurality of pumps, wherein at least one of said plurality of said pumps is disposed in fluidic communication on said plurality of branch catheters.

Example 14

The system of example 8 (as well as subject matter of one or more of any combination of examples 2-7 and 9-13, in whole or in part), wherein said micro flow control device further comprises: a plurality of base catheter valves, wherein at least one of said plurality of base catheter valves is disposed on said base catheter.

Example 15

The system of example 14 (as well as subject matter of one or more of any combination of examples 2-13, in whole or in part), wherein said plurality of branch catheters intercept said base catheter, wherein said interception provides one or more junctures to provide fluidic passage between said base catheter and said plurality of branch catheters.

Example 16

The system of example 15 (as well as subject matter of one or more of any combination of examples 2-14, in whole or in part), wherein at least one of said plurality of base catheter valves is located adjacent to at least one or more of said junctures opposite from said branch catheter.

Example 17

The system of example 16 (as well as subject matter of one or more of any combination of examples 2-15, in whole or in part), wherein at least one of said plurality of branch catheter valves is located adjacent to at least one or more of said junctures opposite from said base catheter.

Example 18

The system of example 8 (as well as subject matter of one or more of any combination of examples 2-7 and 9-17, in whole or in part), wherein said micro flow control device further comprises a plurality of flow sensors, wherein at least one of said plurality of flow sensors is disposed on one or more of said plurality of branch catheters.

Example 19

The system of example 18 (as well as subject matter of one or more of any combination of examples 2-17, in whole or in part), wherein said plurality of valves comprises at least one switch, wherein said at least one switch is configured to adjust flow rate and/or volume of infusate through said branch catheter.

Example 20

The system of example 18 (as well as subject matter of one or more of any combination of examples 2-17 and 19, in whole or in part), further comprising a pump, wherein said pump is disposed in fluidic communication on said base catheter.

Example 21

The system of example 18 (as well as subject matter of one or more of any combination of examples 2-17 and 19-20, in whole or in part), further comprising a plurality of pumps, wherein at least one of said plurality of pumps is disposed on at least one of said plurality of branch catheters.

Example 22

The system of example 1 (as well as subject matter of one or more of any combination of examples 2-21, in whole or in part), wherein the selected site is at least one of the following: tumor or brain.

Example 23

The system of example 1 (as well as subject matter of one or more of any combination of examples 2-22, in whole or in part), wherein the infusate is at least one or more of any combination of the following: therapeutic agent, diagnostic agent, or medication.

Example 24

The system of example 1 (as well as subject matter of one or more of any combination of examples 2-23, in whole or in part), wherein different types of infusate may flow within different said plurality of branch catheters.

Example 25

The system of example 1 (as well as subject matter of one or more of any combination of examples 2-24, in whole or in part), further comprising:
a retainer device, configured to separate and hold each of said plurality of branch catheters as they are independently inserted into the selected site.

Example 26

A distribution system to allow individualized or customized flow control of infusate to each of a plurality of branch catheters to a selected site of a subject. The distribution system may comprise:
a base catheter, configured for providing a passage for the infusate, supplied to the system, said base catheter includes a supply end, a distal end, and an elongated body there between;
said plurality of branch catheters comprise a juncture end, a delivery end, and an elongated body there between, wherein a portion of said elongated body comprises a region having a microporous structure;
a retainer device, configured to separate and hold each of said plurality of branch catheters;
wherein said delivery ends provide an array of said plurality of said branch catheters wherein each of said plurality of said branch catheters, with their said microporous structure, are held by said retainer device and separated from one another by said retainer device while being inserted into the selected site of the subject to a specific inserted position, wherein said microporous structures are configured to allow the infusate to egress from said microporous structure to the selected site; and
a micro flow control device in fluidic communication with each of said plurality of branch catheters; wherein said micro flow control device is configured to control, for each of said plurality of branch catheters, flow rate and volume of the infusate egressing from said microporous structure to the selected site in the specified inserted position.

Example 27

The system of example 26 (as well as subject matter of one or more of any combination of examples 2-25, in whole or in part), wherein said retainer device is in contact with said plurality of branch catheters at said delivery end of said plurality of branch catheters.

Example 28

The system of example 26 (as well as subject matter of one or more of any combination of examples 2-25 and 27, in whole or in part), wherein said retainer device is in contact with said plurality of branch catheters at said elongated body of said plurality of branch catheters.

Example 29

The system of example 26 (as well as subject matter of one or more of any combination of examples 2-25 and 27-28, in whole or in part), where said retainer device is a clamp, holder, lock, coupling, clasp, bracket, press, or vice.

Example 30

A distribution method to allow individualized or customized flow control of infusate to each of a plurality of branch catheters to a selected site of a subject, wherein said distribution method comprises:
providing infusate to a base catheter;
wherein a portion of said elongated body comprises a region having a microporous structure;
independently inserting said branch catheters into the selected site of the subject to a specific inserted position, wherein said microporous structures are configured to allow the infusate to egress from said microporous structure to the selected site; and
controlling each of said plurality of branch catheters, flow rate and volume of the infusate egressing from said microporous structure to the selected site in the specified inserted position.

Example 31

A distribution method to allow individualized or customized flow control of infusate to each of a plurality of branch catheters to a selected site of a subject, wherein said distribution method comprises:
providing infusate to a base catheter;
wherein a portion of said elongated body comprises a region having a microporous structure;
separating and holding each of said plurality of branch catheters with a retaining device;
wherein while holding said plurality of said branch catheters by said retainer device so as to separate from one another and while being inserted into the selected site of the subject to a specific inserted position, and wherein said microporous structures are configured to allow the infusate to egress from said microporous structure to the selected site; and
controlling each of said plurality of branch catheters, flow rate and volume of the infusate egressing from said microporous structure to the selected site in the specified inserted position.

Example 32

The method of using any of the systems (devices, structures, apparatuses, or material) or their components or sub-components provided in any one or more of examples 1-29, in whole or in part.

Example 33

The method of manufacturing any of the systems (devices, structures, apparatuses, or material) or their components or sub-components provided in any one or more of examples 1-29, in whole or in part.

Example 34

The method of Example 30 or 31 and of using any of the systems (devices, structures, apparatuses, or material) or their components or sub-components provided in any one or more of examples 1-29, in whole or in part.

Example 35

The method of Example 30 or 31 and of manufacturing any of the systems (devices, structures, apparatuses, or material) or their components or sub-components provided in any one or more of examples 1-29, in whole or in part.

Example 34

A non-transitory machine readable medium including instructions for providing guided access to subject, which when executed by a machine, cause the machine to perform any of the steps or activities provided in any one or more of examples 30-35. Written instructions for providing guided access to subject, which when executed by a user causes the user to perform any of the steps or activities provided in any one or more of examples 30-35.

REFERENCES

The devices, systems, apparatuses, imaging techniques, compositions, materials, machine readable medium, computer program products, infusate, and methods of various embodiments of the invention disclosed herein may utilize aspects (e.g., devices, systems, apparatuses, imaging techniques, compositions, materials, machine readable medium, computer program products, infustate and methods) disclosed in the following references, applications, publications and patents and which are hereby incorporated by reference herein in their entirety, and which are not admitted to be prior art with respect to the present invention by inclusion in this section:

1. U.S. Pat. No. 9,352,117 B2, O'Day, T., "Infusion Catheter and Methods May 31, 2016.
2. U.S. Pat. No. 8,945,089 B2, Johnson, et al., "Infusion Catheter with Composite Tip", Feb. 3, 2015.
3. U.S. Pat. No. 8,932,270 B2, O'Day, T., "Variable Infusion Length Catheter and Method", Jan. 13, 2015.
4. U.S. Pat. No. 6,594,880 B2, Elsberry, D., "Intraparenchymal Infusion Catheter System", Jul. 22, 2003.
5. U.S. Pat. No. 6,524,300 B2, Meglin, A., "Infusion Catheter with Non-Uniform Drug Delivery Density". Feb. 25, 2003.
6. U.S. Pat. No. 6,093,180, Elsberry, D., "Intraparenchymal Infusion Catheter System" Jul. 25, 2000.
7. U.S. Pat. No. 6,027,487, Crocker, M., "Low Profile Infusion Catheter", Feb. 22, 2000.
8. U.S. Patent Application Publication No. US 2004/0220547 A1, Heruth, K., et al., "Multiple Infusion Section Catheters, Systems, and Methods", Nov. 4, 2004.
9. U.S. Pat. No. 8,216,177 B2, Heruth, K., et al., "Implantable Drug Delivery Systems and Methods", Jul. 10, 2012.
10. U.S. Pat. No. 8,545,477 B2, Burke, P., et al., "Multiple Reservoir Implantable Drug Infusion Device and Method", Oct. 1, 2013.
11. U.S. Pat. No. 8,480,626 B2, Nelson, B., "Infusion Catheter Assembly with Reduced Backflow", Jul. 9, 2013.
12. U.S. Pat. No. 8,808,234 B2, Vogelbaum, M., et al., "Catheter Assembly", Aug. 19, 2014.
13. U.S. Pat. No. 8,979,822 B2, Vogelbaum, M., et al., "Catheter Assembly", Mar. 17, 2015.
14. U.S. Pat. No. 7,069,634 B1, Elsberry, D., "Method for Manufacturing a Catheter", Jul. 4, 2006.
15. U.S. Pat. No. 6,893,429, B2, Petersen, D., "Convection Enhanced Delivery Catheter to Treat Brain and Other Tumors", May 17, 2005.
16. Jahangiri, Arman, et al., "Convection-enhanced delivery in glioblastoma: a review of preclinical and clinical studies", Journal of Neurosurgery 126: 191-200, 2017.
17. U.S. Pat. No. 8,043,281 B2, Heruth, K., et al., "Catheters Incorporating Valves and Permeable Membranes", Oct. 25, 2011.
18. U.S. Patent Application Publication No. US 2006/0229573 A1, Lamborne, A., "Adjustable Infusion Catheter", Oct. 12, 2006.
19. U.S. Pat. No. 8,551,044 B2, Burke, P., et al., "Multiple Reservoir Implantable Drug Infusion Device and Method", Oct. 8, 2013.
20. U.S. Patent Application Publication No. US 2016/0166803 A1, Masi, B., et al., "Systems and Methods for Delivering Chemical and Electrical Stimulation Across one or more Neural Circuits", Jun. 16, 2016.
21. Langer, R., et al., "Ultrathin Needle Can Deliver Drugs Directly to the Brain", MIT News, Anne Trafton, MIT News Office, Jan. 24, 2018.
22. Pham, Windy, Institute for Medical Engineering and Science, "Neural Implants Modulate Microstructures in the Brain with Pinpoint Accuracy", MIT News, Jun. 28, 2018.
23. Prior, Julie, McGovern, Institute for Brain Research, "McGovern Institute Neurotechnology (MINT) program funds three new projects", MIT News, Sep. 18, 2009.
24. U.S. Pat. No. 8,267,905 B2, Lobl, et al., "Apparatus and Method for Delivery of Therapeutic and other Types of Agents", Sep. 18, 2012.
25. International Patent Application Publication No. WO 2007/042999 A2, Hetke, Jamille, et al., "Modular Multichannel Microelectrode Array and Methods of Making Same", Apr. 19, 2007.
26. U.S. Patent Application Publication No. US 2018/0264191 A1, Dagdeviren, et al., "Systems and Methods for Neural Drug Delivery and Modulation of Brain Activity", Sep. 20, 2018.
27. Elias, W. J., Bond, A. E., and Gillies, G. T., "Method and System for Enhanced Imaging Visualization of Deep Brain Anatomy Using Infusion," U.S. Pat. No. 10,159,782, Dec. 25, 2018.
28. Broaddus, W. C., Mahajan, R., and Gillies, G. T., "System and Method for Intracranial Implantation of Therapeutic or Diagnostic Agents," U.S. Pat. No. 9,669,198, Jun. 6, 2017.
29. Broaddus, W. C., Chen, Z. J., and Gillies, G. T., "Coaxial Catheter Systems for Transference of Medium," U.S. Pat. No. 8,728,053, May 20, 2014.
30. Humphrey, J. A. C. and Gillies, G. T., "Blood Flow Bypass Catheters and Methods for the Delivery of Medium to the Vasculature and Body Ducts," U.S. Pat. No. 8,655,798, Feb. 18, 2014.
31. Gillies, G. T., Fillmore H. L., Broaddus, W. C., Evans III, B. M., and Allison, S. W., "Means and Methods for Cytometric Therapies," U.S. Pat. No. 8,406,837, Mar. 26, 2013.
32. Humphrey, J. A. C. and Gillies, G. T., "Blood Flow Bypass Catheters and Methods for the Delivery of Medium to the Vasculature and Body Ducts," U.S. Pat. No. 8,255,193, Aug. 29, 2012.
33. Broaddus, W. C., Chen, Z. J., and Gillies, G. T., "Closure Device for Skull Plates and Related Method Thereof," U.S. Pat. No. 8,226,694, Jul. 24, 2012.
34. Broaddus, W. C., Chen, Z. J., and Gillies, G. T., "Coaxial Catheter Systems for Transference of Medium," U.S. Pat. No. 8,211,083, Jul. 3, 2012.
35. Kucharczyk, J., Gillies, G. T., Broaddus, W. C., and Fillmore, H. L., "Cell Delivery Catheter and Method," U.S. Pat. No. 8,096,984, Jan. 17, 2012.

36. Broaddus, W. C., Chen, Z. J., and Gillies, G. T., "Coaxial Catheter Systems for Transference of Medium," U.S. Pat. No. 7,727,225, Jun. 1, 2010.

37. Kucharczyk, J. and Gillies, G. T., "Catheter Systems for Delivery of Therapeutic Agents and Related Method Thereof," U.S. Pat. No. 7,670,327, Mar. 2, 2010.

38. Gillies, G. T., Hastings, R. N., Garibaldi, J. M., and Broaddus, W. C., "Catheter Navigation within an MR Imaging Device," U.S. Pat. No. 6,834,201, Dec. 21, 2004.

39. Kucharczyk, J. and Gillies, G. T., "Multi-Probe System," U.S. Pat. No. 6,626,902, Sep. 30, 2003.

40. Kucharczyk, J., Broaddus, W. C., Fillmore, H. L., and Gillies, G. T., "Cell Delivery Catheter and Method," U.S. Pat. No. 6,599,274, Jul. 29, 2003.

41. Kucharczyk, J. and Gillies, G. T., "Combined Magnetic Resonance Imaging and Magnetic Stereotaxis Surgical Apparatus and Processes," U.S. Pat. No. 6,298,259, Oct. 2, 2001.

42. Gillies, G. T., Kucharczyk, J., Broaddus, W. C. and Latchaw, R. E., "MR-Visible Medical Device for Neurological Interventions Using Nonlinear Magnetic Stereotaxis and a Method Imaging," U.S. Pat. No. 6,272,370, Aug. 7, 2001.

43. Howard, M. A., Mayberg, M., Grady, M. S., Ritter, R. C., and Gillies, G. T., "Magnetic Stereotactic System for Treatment Delivery," U.S. Pat. No. 6,216,030, Apr. 10, 2001.

44. Howard, M. A., Mayberg, M., Grady, M. S., Ritter, R. C., and Gillies, G. T., "Magnetic Stereotactic System for Treatment Delivery," U.S. Pat. No. 5,779,694, Jul. 14, 1998.

45. Howard, M. A., Mayberg, M., Grady, M. S., Ritter, R. C., and Gillies, G. T., "Magnetic Stereotactic System and Treatment Delivery," U.S. Pat. No. 5,707,335, Jan. 13, 1998.

46. Howard, M. A., Mayberg, M., Grady, M. S., Ritter, R. C., and Gillies, G. T., "Magnetic Stereotactic System for Treatment Delivery," U.S. Pat. No. 5,125,888, Jun. 30, 1992.

47. U.S. patent application Ser. No. 16/181,498, filed Nov. 6, 2018; U.S. Patent Application Publication No. 20190070356, published Mar. 7, 2019.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claims is:

1. A distribution system to allow for flow control of infusate, wherein said system comprises:
    a single base catheter, configured for providing a passage for the infusate, supplied to the system, wherein said base catheter includes a supply end, a distal end, and an elongated body there between;
    a plurality of branch catheters wherein each of said branch catheters comprise a juncture end, a delivery end, and an elongated body there between, wherein a portion of said elongated body comprises a region having a microporous structure;
    wherein said delivery ends of said branch catheters provide an array of said plurality of said branch catheters to allow said infusate to flow from said single base catheter to each of said branch catheters;
    wherein each of said plurality of said branch catheters, with their said microporous structure, are each configured to be independently inserted into a selected site of a subject to a specific inserted position, wherein said microporous structures are configured to allow the infusate to egress from said microporous structure to the selected site;
    wherein said plurality of branch catheters intercept said base catheter at the delivery end of the base catheter and supply ends of said branch catheters, wherein said interception provides one or more junctures to provide fluidic passage between said base catheter and said plurality of branch catheters, and a micro flow control device in fluidic communication with each of said plurality of branch catheters; wherein said micro flow control device is configured to control, for each of said plurality of branch catheters, flow rate and volume of the infusate egressing from said microporous structure to the selected site in the specified inserted position;

where said micro flow control device comprises:
   a plurality of flow sensors, wherein at least one of said plurality of said flow sensors is disposed in fluidic communication on said plurality of branch catheters; and
   a plurality of pumps, wherein at least one of said plurality of pumps is disposed on at least one of said plurality of branch catheters.

2. The system of claim 1, further comprising a controller, microcontroller, processor, or microprocessor in communication with said micro flow control device configured to control operation of said micro flow control device.

3. The system of claim 1, further comprising a reservoir configured for containing a supply of the infusate, and wherein said supply end of said base catheter is in fluidic communication with said reservoir to allow for passage of the infusate to pass through said base catheter.

4. The system of claim 1, wherein at least one or more of said plurality of pumps is a micro pump.

5. The system of claim 1, wherein said micro flow control device comprises:
   a plurality of branch catheter valves, wherein at least one of said plurality of branch catheter valves is disposed on at least one of said plurality of branch catheters.

6. The system of claim 5, wherein said plurality of branch catheter valves are collectively configured as a flow multiplexer (MUX).

7. The system of claim 5, wherein said micro flow control device further comprises:
   a plurality of base catheter valves, wherein at least one of said plurality of base catheter valves is disposed on said base catheter.

8. The system of claim 7, wherein at least one of said plurality of base catheter valves is located adjacent to at least one or more of said junctures opposite from said branch catheter.

9. The system of claim 8, wherein at least one of said plurality of branch catheter valves is located adjacent to at least one or more of said junctures opposite from said base catheter.

10. The system of claim 5, wherein said plurality of branch catheter valves comprises at least one switch, wherein said at least one switch is configured to adjust flow rate and/or volume of infusate through said branch catheter.

11. The system of claim 1, wherein the selected site is at least one of the following: tumor or brain.

12. The system of claim 1, wherein the infusate is at least one or more of any combination of the following: therapeutic agent, diagnostic agent, or medication.

13. The system of claim 1, wherein different types of infusate may flow within different said plurality of branch catheters.

14. The system of claim 1, further comprising:
   a retainer device, configured to separate and hold each of said plurality of branch catheters as they are independently inserted into the selected site.

15. A distribution system for flow control of infusate, wherein said distribution system comprises:
   a single base catheter, configured for providing a passage for the infusate, supplied to the system, wherein said base catheter includes a supply end, a distal end, and an elongated body there between;
   a plurality of branch catheters wherein each of said branch catheters comprise a juncture end, a delivery end, and an elongated body there between, wherein a portion of said elongated body comprises a region having a microporous structure;
   a retainer device, configured to separate and hold each of said plurality of branch catheters;
   wherein said delivery ends of said branch catheters provide an array of said plurality of said branch catheters to allow said infusate to flow from said single base catheter to each of said branch catheters;
   wherein each of said plurality of said branch catheters, with their said microporous structure, are held by said retainer device and separated from one another by said retainer device while being inserted into a selected site of a subject to a specific inserted position, wherein said microporous structures are configured to allow the infusate to egress from said microporous structure to the selected site;
   wherein said plurality of branch catheters intercept said base catheter at the delivery end of the base catheter and supply ends of said branch catheters, wherein said interception provides one or more junctures to provide fluidic passage between said base catheter and said plurality of branch catheters; and
   a micro flow control device in fluidic communication with each of said plurality, of branch catheters; wherein said micro flow control device is configured to control, for each of said plurality of branch catheters, flow rate and volume of the infusate egressing from said microporous structure to the selected site in the specified inserted position;
   where said micro flow control device comprises:
      a plurality of flow sensors, wherein at least one of said plurality of said flow sensors is disposed in fluidic communication on said plurality of branch catheters; and
      a plurality of pumps, wherein at least one of said plurality of pumps is disposed on at least one of said plurality of branch catheters.

16. The system of claim 15, wherein said retainer device is in contact with said plurality of branch catheters at said delivery end of said plurality of branch catheters.

17. The system of claim 15, wherein said retainer device is in contact with said plurality of branch catheters at said elongated body of said plurality of branch catheters.

18. The system of claim 15, where said retainer device is a clamp, holder, lock, coupling, clasp, bracket, press, or vice.

19. The system of claim 15, further comprising a controller, microcontroller, processor, or microprocessor in communication with said micro flow control device configured to control operation of said micro flow control device.

20. The system of claim 15, further comprising a reservoir configured for containing a supply of the infusate, and wherein said supply end of said base catheter is in fluidic communication with said reservoir to allow for passage of the infusate to pass through said base catheter.

21. The system of claim 15, wherein at least one or more of said plurality of pumps is a micro pump.

22. The system of claim 15, wherein said micro flow control device comprises:
    a plurality of branch catheter valves, wherein at least one of said plurality of branch catheter valves is disposed on at least one of said plurality of branch catheters.

23. The system of claim 22, wherein said plurality of branch catheter valves are collectively configured as a flow multiplexer (MUX).

24. The system of claim 22, wherein said micro flow control device further comprises:
    a plurality of base catheter valves, wherein at least one of said plurality of base catheter valves is disposed on said base catheter.

25. The system of claim 24, wherein at least one of said plurality of base catheter valves is located adjacent to at least one or more of said junctures opposite from said branch catheter.

26. The system of claim 25, wherein at least one of said plurality of branch catheter valves is located adjacent to at least one or more of said junctures opposite from said base catheter.

27. The system of claim 22, wherein said plurality of branch catheter valves comprises at least one switch, wherein said at least one switch is configured to adjust flow rate and/or volume of infusate through said branch catheter.

28. The system of claim 15, wherein the selected site is at least one of the following: tumor or brain.

29. The system of claim 15, wherein the infusate is at least one or more of any combination of the following: therapeutic agent, diagnostic agent, or medication.

30. The system of claim 15, wherein different types of infusate may flow within different said plurality of branch catheters.

* * * * *